US005840277A

United States Patent [19]

Ghio et al.

[11] Patent Number: 5,840,277

[45] Date of Patent: Nov. 24, 1998

[54] TREATMENT OF CHRONIC PULMONARY INFLAMMATION

[75] Inventors: Andrew J. Ghio, Durham, N.C.; Thomas P. Kennedy, Richmond, Va.

[73] Assignee: Charlotte Hospital Authority, Charlotte, N.C.

[21] Appl. No.: 632,275

[22] Filed: Apr. 15, 1996

Related U.S. Application Data

[63] Continuation-in-part of Ser. No. 413,699, Mar. 30, 1995, which is a continuation-in-part of Ser. No. 219,770, Mar. 29, 1994, Pat. No. 5,474,760, which is a continuation-in-part of Ser. No. 299,316, Aug. 31, 1994, Pat. No. 5,512,270, which is a continuation-in-part of Ser. No. 39,732, Mar. 30, 1993, abandoned.

[51] Int. Cl.$^6$ .......................... A61K 9/12; A61K 31/765

[52] U.S. Cl. ..................... 424/45; 424/78.37; 424/78.05; 514/828; 514/851

[58] Field of Search ............................... 435/7.1; 424/45, 424/78.05, 78.06, 78.08, 78.37; 514/887, 828, 851

[56] References Cited

U.S. PATENT DOCUMENTS

| | | | |
|---|---|---|---|
| 2,454,541 | 11/1948 | Bock et al. | 525/507 |
| 3,663,230 | 5/1972 | Sato et al. | 430/550 |
| 4,039,669 | 8/1977 | Beyler et al. | 514/178 |
| 4,826,821 | 5/1989 | Clements | 514/78 |
| 4,944,941 | 7/1990 | Ammann | 424/85.5 |
| 5,110,806 | 5/1992 | Clements | 514/78 |
| 5,134,129 | 7/1992 | Lichtenberger | 514/78 |
| 5,145,684 | 9/1992 | Liversidge et al. | 424/489 |
| 5,259,963 | 11/1993 | Wiedemann | 510/321 |
| 5,399,363 | 3/1995 | Liversidge et al. | 424/490 |
| 5,474,760 | 12/1995 | Ghio et al. | 424/45 |
| 5,512,270 | 4/1996 | Ghio et al. | 424/45 |

OTHER PUBLICATIONS

Thomassen, Regulation Of Human Alveolar Macrophage Inflammatory Cytokines By Tyloxapol: A Component Of The Synthetic Surfactant Exosurf, *Clin. Immonol. Immunopathol.*, vol. 77, No. 2, pp. 201–205, (Nov. 1995).

Harold N. Glassman, Hemolytic Activity Of Some Nonionic Surface–Active Agents,*Science*, vol. III, Jun. 23, 1950, pp. 688–689.

Oliver H. Lowry, Nira J. Rosebrough, A. Lewis Farr and Rose J. Randall, Protein Measurement With The Folin Phenol Reagent,*Journal of Biological Chemistry*, vol. 193, 1951, pp. 265–275.

Dr. J.W. Cornforth, Dr. P. D'Arcy Hart, R. J. W. Rees and J. A. Stock, Antituberculous effect Of Certain Surface–Active Polyoxyethylene Ethers In Mice,*Nature*, vol. 168, July 28, 1951, pp. 150–153.

Maurice L. Tainter, M.D., Frederick C. Nachod, Ph.D. and Joseph G. Bird, M. D., Alevaire As A Mucolytic Agent, *The New England Journal Of Medicine*, vol. 253, Nov. 3, 1995, pp. 764–767.

K.N.V. Palmer, M.A., M.D. Camb., M.R.C.P., The Effect Of An Aerosol Detergent In Chronic Bronchitis,*The Lancet*, Mar. 23, 1957, pp. 611–613.

John W. Polk, M.D. and Marcelino Medina, M.D., A Comparative Study of Alevaire And A New Mucolytic Agent, Acumist In Postoperative Patients,*The Eye, Ear, Nose and Throat Monthly*,vol. 49, Jul. 1970, pp. 321–324

M.V. Pimm and R. W. Baldwin, Influence Of ICRF 159 and Triton WR 1339 On Metastases Of A Rat Epithelioma, *The British Journal Of Cancer*,vol. 31, No. 1, Jan. 1975, pp. 62–67.

Kunihisa Hashimoto, Senji Miura and Chigashi Suzuki, Antimetastatic Effect Of Triton WR 1339, a Nonionic Detergent, On Rat Ascites Tumors, *The Tohoku Journal Of Experimental Medicine*, vol. 128, No. 3, Jul. 1979, pp. 259–265.

Robert A. Floyd, Julia J. Watson and Peter K. Wong, *Sensitive Assay Of Hydroxyl Free Radical Formation Utilizing High Pressure Liquid Chromatography With Electrochemical Detection Of Phenol And Salicylate Hydroxylation Products, Journal Of Biochemical And Biophysical Methods*, vol. 10, 1984, pp. 221–235.

Julio F. Turrens, James D. Crapo and Bruce A. Freeman, Protection Against Oxygen Toxicity By Intravenous Injection Of Liposome–Entrapped Catalase And Superoxide Dismutase, *Journal Of Clinical Investigation*, vol. 73, Jan. 1984, pp. 87–95.

(List continued on next page.)

*Primary Examiner*—David Guzo

*Attorney, Agent, or Firm*—The Bell Seltzer Intellectual Law Firm of Alston & Bird, LLP

[57] ABSTRACT

A method and medicant for the inhibition of activation of the nuclear transcription NF-κB comprising administering an effective amount of a compound of the formula:

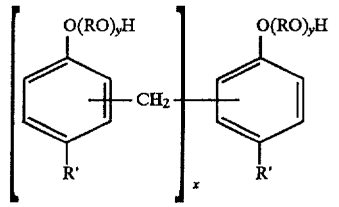

where R=ethylene, R'=$C_4$ to $C_{14}$ straight chain or branched alkyl, x is greater than 1, and y=8 to 18 is provided. The medicant is preferably administered by aerosolization into the mammalian respiratory system. The medicant may also be applied to the mammalian skin. Preferably the medicant includes a physiologically acceptable carrier which may be selected from buffered saline, isotonic saline, normal saline, petroleum-based ointments and U.S.P. cold cream. There is further provided a method wherein said medicant includes an anti-inflammatory steroid. In addition a method and medicant for treating cutaneous inflammatory disorders, inhibiting the secretion of the pro-inflammatory cytokines TNF, IL-1, IL-6, IL-8 and the growth factor GM-CSF is provided.

17 Claims, 8 Drawing Sheets

OTHER PUBLICATIONS

Robert A. Floyd, Julia J. Watson and Peter K. Wong, Use Of Salicylate With High Pressure Liquid Chromatography And Electrochemical Detection (LCED) As A Sensitive Measure Of Hydroxyl Free Radicals In Adriamycin Treated Rats, *Journal Of Free Radicals In Biology & Medicine*, vol. 2, 1986, pp. 13–18.

M.F. McCarty,*An Antithrombotic Role For Nutritional Antioxidants: Implications For Tumor Metastasis And Other Pathologies,Med–Hypotheses,*Apr. 1986, pp. 345–57.

Eiko Kondo and Koomi Kanai, Triton WR-1339 As a Biological–Response Modifier In Mycobacterial Infection, *Japan Journal Medical Science Biology,* vol. 39, 1986, pp. 35–47.

Sadis Matalon, Bruce A. Holm and Robert H. Notter, Mitigation Of Pulmonary Hyperoxic Injury By Administration Of Exogenous Surfactant,*American Physiological Society,*1987, pp. 756–761.

Robert A. Greenwald,*Determination Of HOC1 Production By Micloperoxidase, CRC Handbook Of Methods For Oxygen Radical Research,*1987, p. 300.

W.H. Tooley, J.A. Clements, K. Muramatsu, C.L. Brown and M.A. Schlueter, Lung Function In Prematurely Delivered Rabbits Treated With A Synthetic Surfactant,*Am Rev Respir Dis,*Sep. 1987, pp. 651–656.

Robert H. Notter, Biophysical Behavior Of Lung Surfactant: Implications For Respiratory Physiology And Pathophysiology, *Seminars In Perinatology*, vol. 12, No. 3, Jul. 1988, pp. 180–212.

R. Randall Baker, Bruce A. Holm, Peter C. Panus and Sadis Matalon, *Development Of $O_2$ Tolerance In Rabbits With No Increase In Antioxidant Enzymes, American Physiological Society*, 1989, pp. 1679–1684.

Barry Halliwell and John M.C. Gutteridge, Role Of Free Radicals And Catalytic Metal Ions In Human Disease: An Overview, *Methods In Enzymology*, vol. 186, 1990, pp. 1–83.

Michael I. Lethem, Stuart L. James and Christopher Marriott, The Role Of Mucous Glycoproteins In The Rheologic Properties Of Cystic Fibrosis Sputum, *Am Rev Respir Dis,* 1990, pp. 1053–1058.

H. Wiseman, M. Cannon, H.R. Arnstein and D.J. Barlow, The Structural Mimicry Of Membrane Sterols By Tamoxifen: Evidence From Cholesterol Coefficients And Molecular–Modelling For Its Action As A Membrane Anti–Oxidant And An Anti–Cancer Agent, *Biochim–Biophys–Acta.*, Mar. 20, 1992, pp. 197–202.

Andrew J. Ghio, Thomas P. Kennedy, A. Richard Whorton, Alvin L. Crumbliss, Gary E. Hatch and John R. Hoidal, Role of Surface Complexed Iron In Oxidant Generation And Lung Inflammation Induced By Silicates,*American Journal Of Physiology, Lung Cellular And Molecular Physiology 7,* vol. 263, Jun. 29, 1992, pp. L511–L518.

H. Wiseman, C. Smith, B. Halliwell, M. Cannon, H.R. Arnstein and M.S. Lennard, Droloxifene (3–Hydroxytamoxifen) Has Membrane Antioxidant Ability: Potential Relevance To Its Mechanism Of Therapeutic Action In Breast Cancer, *Cancer–Lett.*, Sep. 14, 1992, pp. 61–68.

Hong–Suk Kim, Soon–Kyu Chung and Jin Jung, Reevaluation Of The Effect Of Triton X–100 On The Assay Of Superoxide Radical By The Nitrobluetetrazolium Reduction Method, *Hanguk Nonghwahak Hoechi* (*J. Korean Agric. Chem. Soc.*), 1993, pp. 364–369.

Correspondence from Carolann W. Hootan, Department Of Health & Human Services, regarding Alevaire, dated May 27, 1994, including brochure of ALEVAIRE®dated Nov. 1965.

André Cantin and Donald E. Woods, Protection By Antibiotics Against Myeloperoxidase–Dependent Cytotoxicity To Lung Epithelial Cells In Vitro, *J. Clin. Invest.,* vol. 91, Jan. 1993, pp. 38–45.

Okezie I. Aruoma,Deoxyribose Assay For Detecting Hydroxyl Radicals, *Methods In Enzymology,* vol. 233, 1994, pp. 57–82.

Andrew J. Ghio, Philip J. Fracica, Stephen L. Young and Claude A. Piantadosi,Synthetic Surfactant Scavenges Oxidants And Protects Against Hyperoxic Lung Injury, *Journal Of Applied Physiology,* vol. 77, 1994, pp. 1217–1223.

Carol A. Vasconcellos, Phillip G. Allen, Mary Ellen Wohl, Jeffrey M. Drazen, Paul A. Janmey and Thomas P. Stoesel, Reduction In Viscosity Of Cystic Fibrosis Sputum In Vitro By Gelsolin, *Science*, vol. 263, Feb. 16, 1994, pp. 969–971.

Henry J. Fuchs, M.D., Drucy S. Borowitz, M.D., David H. Christiansen, Dr. P.H., Edward M. Morris, Pharm D., Martha L. Nash, R.N., Bonnie W. Ramsey, M.D., Beryl J. Rosenstein, M.D., Arnold I. Smith, M.D. and Mary Ellen Wohl, M.D., Effect Of Aerosolized Recombinant Human DNase On Exacerbations of Respiratory Symptoms And On Pulmonary Function In Patients With Cystic Fibrosis, *The New England Journal Of Medicine,* vol. 331, No. 10, Sep. 1994, pp. 637–642.

Bonnie W. Ramsey, M.D., Henry L. Dorrin, M.D., Jay D. Eisenberg, M.D., Ronald L. Gibson, M.D., Ph.D., Evan R. Harwood, M.D., Richard M. Kravitz, M.D., Daniel V. Scridlow, M.D., Robert W. Wilmott, M.D., Susan J. Astley, Ph.D., Mary Ann McBurne, M.S., Kim Wentz, M.D., M.P.H., and Arnold I. Smith, M.D., Efficacy Of Aerosolized Tobramycin In Patients With Cystic Fibrosis, *The New England Journal Of Medicine,* vol. 328, No. 24, pp. 1740–1746.

TREATMENT OF CHRONIC PULMONARY INFLAMMATION

CROSS-REFERENCE TO RELATED APPLICATIONS

This application is a Continuation-in-Part of U.S. application Ser. No. 08/413,699, filed Mar. 30, 1995; which is a Continuation-in-Part of U.S. application Ser. No. 08/219,770, now U.S. Pat. No. 5,474,760, filed on Mar. 29, 1994 issued Dec. 12, 1995; which is a Continuation-In-Part of U.S. application Ser. No. 299,316, filed Aug. 31, 1994 and now U.S. Pat. No. 5,512,270; which is a Continuation-in-Part of U.S. application Ser. No. 08/039,732, filed Mar. 30, 1993, now abandoned.

BACKGROUND OF THE INVENTION

1. Field of the Invention

The present invention relates to the use of alkylaryl polyether alcohol polymers in the treatment of chronic inflammation. More particularly, the present invention relates to the use of alkylaryl polyether alcohol polymers to reduce the activation of nuclear factor kappa B (NF-κB) and inhibit the secretion of pro-inflammatory cytokines TNF-alpha (TNF-α), interleukin-1 beta (IL-1β), interleukin-6 (IL-6), interleukin-8 (IL-8) and the growth factor granulocyte macrophage colony stimulating factor (GM-CSF).

2. The Prior Art

Discussion of Oxidant-Mediated Injury

Oxygen is life-giving to aerobic plants and animals who depend on it for energy metabolism. It can also be lethal to those same organisms when it is altered from its stable dioxygen ($O_2$) state to any one of three partially reduced species: a) the one electron reduced form superoxide anion ($°O_2^-$) ; the two electron reduced form hydrogen peroxide ($H_2O_2$); or the deadly three electron reduced form the hydroxyl radical (°OH). In biologic systems $O_{2-}$ and $H_2O_2$ are metabolic byproducts of a host of enzymes (oxygenases) that use oxygen as a cofactor. $H_2O_2$ is also produced from $°O_2$— by the enzymatic action of superoxide dismutases. However, °OH is generally produced only when $°O_2$— and $H_2O_2$ interact with transitional ions of metals such as iron, copper, nickel or vanadium in dangerous cyclical redox reactions:

$$Fe^{3+}+°O_2— \rightarrow Fe^{2+}+O_2$$

$$Fe^{2+}+H_2O_2 \rightarrow Fe^{3+}+°OH+^-OH$$

The above reactions are termed the superoxide-driven Fenton reaction common in biological systems. The Fenton reaction can also be initiated by other reducing substances such as ascorbate in the presence of ferric iron and $H_2O_2$.

While $°O_2$— and $H_2O_2$ are each toxic for biological systems, °OH (and its alternant hypothesized form the ferryl intermediate $FeO^{2+}$) is a highly reactive species that can oxidize unsaturated membrane lipids, damage cellular proteins and cause mutagenic strand breaks in DNA. To prevent injury from partially reduced $O_2$ species under normal conditions, cells have evolved an elaborate system of antioxidant enzymes (superoxide dismutase, catalase, glutathione peroxidase) and antioxidant molecules (gluathione, alpha-tocopherol, beta carotene). However, when production of partially reduced $O_2$ species exceeds capacity of antioxidant defenses to contain them, oxidant injury occurs.

A growing number of mammalian disease entities are now thought to be related to overproduction of partially reduced $O_2$ species, including the reperfusion injury syndromes myocardial infarction and stroke, adult respiratory distress syndrome, oxygen toxicity of the lung, lung injury from asbestos, Parkinson's disease, thermal and solar burns of the skin, injury to the gastrointestinal tract from nonsteroidal anti-inflammatory agents and airway diseases such as chronic bronchitis, asthma and cystic fibrosis (see Table IV, page 60, B. Halliwell and J. M. C. Gutteridge. *Methods in Enzymology* (1990) 186:1–85). Treatment of these conditions is increasingly directed either toward strategies that prevent enzymatic production of partially reduced $O_2$ species and to the introduction of exogenous antioxidant compounds that restore oxidant-antioxidant balance in biologic and chemical systems. More recently, as will be outlined below, treatment of inflammation in many of these conditions has been directed toward interrupting activation of the transcription factors mediating the genetic expression of pro-inflammatory cytokines important in the pathogenesis of these conditions.

Discussion of Transcription Factors and Cytokines

Transcription factors are cellular proteins that bind to regulatory sequences of genes and increase or decrease the rate of gene transcription. By affecting the rate of gene transcription, transcription factors play a critical role in regulation of cell function during health and disease. Among the most important transcription factors in disease are those that regulate expression of the genes for pro-inflammatory cytokines. These cytokines are secreted cellular proteins that dramatically affect the behavior of other cells. As examples, the cytokine TNF-α causes weight loss in patients with tumors or chronic infections, produces cellular death and is thought to be an important mediator of septic shock. The cytokine IL-1β mediates fever, and shares many of the properties of TNF. The cytokine IL-8 (and its close relatives such as RANTES) is a potent chemotactic signal aiding in the recruitment of inflammatory cells such as neutrophils. The cytokine GM-CSF signals the bone marrow to produce more inflammatory cells, activates those cells once produced and lengthens their survival.

These cytokines play important roles in mediating the pathogenesis of such inflammatory diseases as cystic fibrosis, chronic bronchitis, asthma and viral infections, among many others (T. L. Bonfield, et al. "Inflammatory cytokines in cystic fibrosis lungs". *American Journal of Respiratory and Critical Care Medicine* (1996) In Press; N. G. McElvaney, et al. "Modulation of airway inflammation in cystic fibrosis. In vivo suppression of interleukin-8 levels on the respiratory epithelial surface by aerosolization of recombinant secretory leukoprotease inhibitor". *Journal of Clinical Investigation* (1992) 90:1296–1301; K. D. Pfeffer, et al. "Expression and regulation of tumor necrosis factor in macrophages from cystic fibrosis patients". *American Journal of Respiratory, Cell and Molecular Biology* (1993) 9:511–519; G. Williams and B. P. Giroir. "Regulation of cytokine gene expression: Tumor necrosis factor, interleukin-1, and the emerging biology of cytokine receptors". *New Horizons* (1995) 3:276–287; C. A. Dinarello. "Role of interleukin-1 and tumor necrosis factor in systemic responses to infection and inflammation". In *Inflammation: Basic Principles and Clinical Correlates,* second edition. J. I Gallin, I. M. Goldstein, and R. Snyderman, editors. Raven Press, Ltd., New York (1992) p. 211–232; W. C. Greene. "The interleukins". In *Inflammation: Basic Principles and Clinical Correlates,* second edition. J. I. Gallin, I. M. Goldstein, and R. Snyderman, editors. Raven Press, Ltd., New York (1992) p. 233–245; M. Baggiolini, et al.

"Interleukin-8 and related chemotactic cytokines". In *Inflammation: Basic Principles and Clinical Correlates,* second edition. J. I. Gallin, I. M. Goldstein, and R. Snyderman, editors. Raven Press, Ltd., New York (1992) p. 247–263; D. W. Golde and G. C. Baldwin. "Myeloid growth factors". In *Inflammation: Basic Principles and Clinical Correlates,* second edition. J. I. Gallin, I. M. Goldstein, and R. Snyderman, editors. Raven Press, Ltd., New York (1992) p. 291–301; R. J. Horwitz and W. W. Busse. "Inflammation and asthma". *Clinics in Chest Medicine* (1995) 16:583–602).

These cytokines share regulation of their expression by the transcription factor Nuclear Factor kappa-B (NF-κB), a particularly important transcription factor mediating inflammatory events (U. Siebenlist, G. Granzuso and R. Brown. "Structure, regulation and function of NF-κB". *Annual Review of Cell Biology* (1994) 10:405–455). NF-κB is also an important transcriptional regulator of chemokines such as RANTES (U. Siebenlist, G. Granzuso and R. Brown. "Structure, regulation and function of NF-κB". *Annual Review of Cell Biology* (1994) 10:405–455) and of inducible nitric oxide synthase (iNOS) (P. J. Nelson, et al. "Genomic organisation and transcriptional regulation of the RANTES chemokine gene". *Journal of Immunology* (1993) 151:2601–2612), the enzyme producing nitric oxide (NO°), a critical oxidant chemical produced as part of the pathogenesis of septic shock. NF-κB is present in the cytoplasm in an inactive form complexed to an inhibitory protein IκB. A number of events, yet to be completely characterized, cause IκB to dissociate from NF-κB in the cytoplasm. Free NF-κB then localizes to the nucleus, where it binds to a specific κB recognition site in the promoter region of target genes, prompting their expression. NF-κB is activated by a number of stimuli, including cytokines themselves, and by lipopolysaccharide (LPS) (U. Siebenlist, G. Granzuso and R. Brown. "Structure, regulation and function of NF-κB". *Annual Review of Cell Biology* (1994) 10:405–455). NF-κB is also activated by oxidants such as hydrogen peroxide (M. Meyer, R. Schreck, and P. A. Baeverie. "$H_2O_2$ and antioxidants have opposite effects on the activation of NF-κB and AP-1 in intact cells: AP-1 as secondary antioxidant response factor". *EMBO Journal* (1993) 12:2005–2015), suggesting that it may be an oxidant-stress responsive transcription factor. Conversely, some of the most potent inhibitors of NF-κB activation are compounds which can also act as antioxidants. A few, but not most, antioxidants prevent activation of NF-κB by LPS, prevent increases in corresponding messenger RNAs for inflammatory cytokines and decrease levels of TNF and IL-1 in the circulation following LPS injection (E. M. Eugui, et al. "Some antioxidants inhibit, in a coordinate fashion, the production of tumor necrosis factor α, IL-1β and IL-6 by human peripheral blood mononuclear cells". *International Journal of Immunology* (1993) 6:409–422; R. Schreck, et al. "Dithiocarbamates as potent inhibitors of nuclear factor κB activation in intact cells". *Journal of Experimental Medicine* (1992) 175:1181–1194). However, the few antioxidants known to inhibit NF-κB activation share no common structural similarity distinguishing them from those antioxidants that fail to prevent activation of NF-κB (see Eugui, above), preventing one skilled in the art from predicting which antioxidant compounds will and which will not favorably reduce NF-κB activation as a strategy of ameliorating inflammatory events in disease.

Another class of compounds known to inhibit NF-κB activation are anti-inflammatory steroids. Steroids act by combining in the cytoplasm with an intracellular protein called the Glucocorticoid Receptor (GR). Previously, the anti-inflammatory action of steroids was thought to occur exclusively as a result of passage of the GR-steroid complex to the nucleus, where the complex attaches to and influences regulatory gene regions called Glucocorticoid Responsive Elements (GREs). However, recently it has been shown that a major mechanism of anti-inflammatory steroid activity is inhibition of NF-κB (I. M. Adcock, et al. "Effects of glucocorticoids on transcription factor activation in human peripheral blood mononuclear cells". *American Journal of Physiology* (1995) 268 (*Cell Physiology* 37):C331–C338). The GR-steroid complex prevents activation of NF-κB by directly interacting with free NF-κB in the cytoplasm, preventing NF-κB from translocating to the nucleus (A. Ray and K. E. Prefontaine. "Physical association and functional antagonism between the p65 subunit of transcription factor NF-κB and the glucocorticoid receptor". *Proceedings of the National Academy of Sciences, USA* (1994) 91:752–756). However, the GR-steroid complex accomplishes inhibition of NF-κB by mutual repression. By combining with free NF-κB in the cytoplasm, it too is kept from translocating to the nucleus to up-regulate other anti-inflammatory events. Indeed, mutual repression is thought to explain in part the phenomenon of steroid resistance in severe asthmatics. IL-1, IL-6, TNF and other pro-inflammatory cytokines secreted in the airway during an asthma attack increase cellular activation of NF-κB, providing more NF-κB subunits to bind GR-steroid complexes, reducing the amount of GR-steroid complex available to translocate to the nucleus (P. J. Barnes, A. P. Greening and G. K. Crompton. "Glucocorticoid resistance in asthma". *American Journal of Respiratory and Critical Care Medicine* (1995) 152:S125–S142).

Discussion of Alkylaryl Polyether Alcohol Polymers, Including Tyloxapol

Antioxidants are compounds that can be easily oxidized to stable chemical forms. They can protect chemical and biologic systems by sacrificing themselves to oxidation in preference to oxidation of critically important chemical and biological molecules. Not all oxidizable compounds can perform antioxidant function. To successfully protect chemical and biologic systems from oxidants, the antioxidant must have a higher reactivity for the oxidant than the chemical or biologic molecule which it seeks to protect. To protect the desired chemical and biologic system from oxidation, it is also necessary for the antioxidant to partition itself adjacent to the molecule to be protected. As an example, a molecule to be protected within the lipid bilayer of plasma, endosomal or nuclear membranes might be best protected by an antioxidant with, at least in part, a lipophilic structure, so that it is partitioned to or near the lipid portion of the membrane, adjacent to the molecule needing protection from oxidation.

We have recently shown that a previously known class of drugs, the alkylaryl polyether alcohol polymers, are potent antioxidants useful in the treatment of mammalian diseases (U.S. Pat. No. 5,474,760 issued Dec. 12, 1995 and U.S. Ser. No. 08/039,732 filed Mar. 30, 1993, now abandoned both to Ghio, Kennedy and Piantadosi). Alkylaryl polyether alcohol polymers are used commercially as surface active detergents and wetting agents (U.S. Pat. No. 2,454,541 to Bock and Rainey). The best known of this class is tyloxapol, a polymer of 4-(1,1,3,3-tetramethylbutyl)phenol with formaldehyde and oxirane. However, other compounds in the class, sharing the properties of tyloxapol, are well known in the art (J. W. Cornforth, et al. "Antituberculous effect of certain surface-active polyoxyethylene ethers in mice". *Nature* (1951) 168:150–153).

Tyloxapol is relatively nontoxic and does not hemolyze red blood cells in a thousand times the concentrations at which other detergents are hemolytic (H. N. Glassman. "Hemolytic activity of some nonionic surface-active agents". *Science* (1950)111:688–689). Tyloxapol has been used in human pharmacologic formulations for over 30 years (M. L. Tainter, et al. "Alevaire as a mucolytic agent". *New England Journal of Medicine* (1955) 253:764–767). For instance, a composition sold by Winthrop Laboratories (a division of Sterling Drug, Inc.) and by Breon Laboratories (subsidiary of Sterling Drug, Inc.) under the trademark "ALEVAIRE", containing 0.125% "SUPERINONE" (brand of tyloxapol) in combination with 2% sodium bicarbonate and 5% glycerin, had been marketed for about 30 years for treatment of mucous secretions in patients with diseases and disorders such as chronic bronchitis, croup, pertussis, and poliomyelitis. (See, for example, a product brochure entitled "ALEVAIRE" Detergent Aerosol for Inhalation" (November, 1961) distributed by Breon Laboratories.).

However, in December of 1981, "ALEVAIRE" was withdrawn by the Food and Drug Administration for lack of efficacy for treatment of mucous secretions in patients with diseases and disorders such as chronic bronchitis, croup, pertussis, and poliomyelitis because it was found that there was no evidence that the tyloxapol in "ALEVAIRE" had any effect on secretions in the lung from diseases such as chronic bronchitis other than that of water in thinning secretions by simple dilution, and that papers in the manufacturer's bibliography were based on clinical impression and did not reflect adequate controls. (See, letter dated May 27, 1994 to Dr. Thomas Kennedy, one of the co-inventors of the present application, from Ms. Carolann W. Hooton, Chief, Freedom of Information Office, Center for Drug Evaluation and Research, Department of Health & Human Services, Public Health Service, Food and Drug Administration, Rockville, Md.).

Surprisingly, the present inventors have found that alkylaryl polyether alcohol polymers of the class typified by tyloxapol, are potent inhibitors of the activation of NF-κB, thereby preventing cellular production of pro-inflammatory cytokines.

Synopsis of Background Discussion

Inflammation in a multitude of diseases is mediated by activation of the transcription factor NF-κB, which in turn causes an increase in cellular production of pro-inflammatory cytokines such as TNF, IL-1, IL-6, IL-8 and the growth factor GM-CSF, and an increase in critical cellular enzymes, such as inducible nitric oxide synthase (iNOS). The current treatment available to prevent activation of NF-κB and subsequent cytokine secretion is anti-inflammatory glucocorticoids. Recently a few, but not most, antioxidants have been found to also inhibit NF-κB.

It is theoretically possible to synthesize a multitude of compounds with antioxidant properties. However, there is no predictable structural similarity among the few agents shown to prevent NF-κB activation. Thus, the demonstration that a compound shows antioxidant activity would not, in of itself, predict that the same compound would also inhibit NF-κB activation and secretion of pro-inflammatory cytokines. Also, the factor limiting use of antioxidants as treatments in biologic systems is the inherent toxicity of many antioxidant compound themselves. Likewise, anti-inflammatory cortosteroids are potent inhibitors of NF-κB, but their use as such is severely limited by the well-known side effects of corticosteroids, including glucose intolerance, hypertension, bone resorption, weight gain and cataracts. Thus, it is a major advantage to discover that a class of commonly used and nontoxic ingredients in medicinal pharmacologic preparations are not only potent antioxidants, but also potent inhibitors of NF-κB activation. Not only can such compounds be used as treatments for diseases where antioxidants might be predicted to be of value, but they can be used as treatments for NF-κB mediated inflammatory conditions without themselves causing toxicity to biologic systems.

SUMMARY OF THE INVENTION

It is an object of the present invention to provide a method to inhibit oxidant chemical reactions caused by partially reduced $O_2$ species.

It is a further object of the present invention to provide a method to protect mammalian tissues against injury from partially reduced $O_2$ species.

It is a further object of the present invention to provide a method and medicament to protect from airway injury by HOCl/OCl, which for convenience, is referred to herein also as HOCl.

It is a further object of the present invention to provide a method for inhibiting oxidant chemical reactions caused by partially reduced $O_2$ species by aerosol treatment with the therapeutic agent.

It is a further object of the present invention to provide a method for inhibiting oxidant chemical reactions caused by partially reduced $O_2$ species by topical application of the therapeutic agent to the skin.

It is a further object of the present invention to provide a method and medicament for the inhibition of activation of the transcription factor NF-κB (thus ameliorating the pro-inflammatory cellular events evoked by activating genes controlled by this regulatory cell protein).

It is a further object of the present invention to provide a method and medicament for the inhibition of the cytokines TNF, IL-1, IL-6 and IL-8 and the growth factor GM-CSF.

It is a further object of the present invention to provide a method and medicament for preventing steroid resistance in asthma and other diseases by blocking activation of the transcription factor NF-κB, thereby preventing binding and mutual repression of the glucocorticoid receptor complex by active NF-κB present in the cytoplasm.

It is an advantage of the present invention that the therapeutic agent is produced from a toxicologically characterized class of compounds with low toxicologic potential to biologic systems.

In accordance with these objects and the principles of this invention, it has been found that alkylaryl polyether alcohol polymers, such as tyloxapol, are useful as treatment agents for inhibiting activation of the transcription factor NF-κB, and as inhibitors of cellular secretion of the cytokines TNF, IL-1, IL-6 and IL-8 and the growth factor GM-CSF. Administration may be the same as described in U.S. Pat. No. 5,474,760.

The present invention provides a medicament for a medicament for the inhibition of injurious effects of partially reduced $O_2$ species in chemical and biologic systems comprising as a treatment an effective amount of alkylaryl polyether alcohol polymer of the formula:

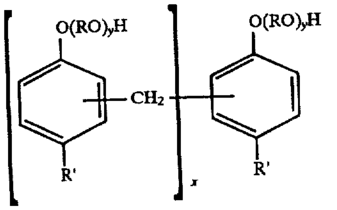

where R=ethylene, R'=$C_4$ to $C_{14}$ straight or branched alkyl, x is greater than 1, and y=2 to 18, effective to inhibit oxidant chemical reactions caused by the oxidant species in the mammal, thereby treating the mammalian disease entities.

Also, the alkylaryl polyether alcohol polymer is thought effective by virtue of having a hydrophobic portion of structure placing it in lipid membranes, and also a hydrophilic portion of structure allowing it to interact with the external environment or cytosolic compartment of the cell.

Also, the present invention provides a method and medicament comprising administering to a mammal a treatment effect among of tyloxapol and related alkylaryl polyether alcohol polymers.

In one embodiment of the invention, the medicament is directly instilled into the respiratory system and administered by aerosolization. In this embodiment, the medicament preferably includes a physiologically acceptable carrier which may be selected from the group consisting of physiologically buffered saline, isotonic saline, and normal saline and an additional treatment effective amount of cetyl alcohol. The pH of the alkylaryl polyether alcohol polymer and carrier mixture is preferably greater than 6.5 but equal to or less than 7.4.

In other embodiments of the invention, this medicament is applied topically to the skin. In this embodiment, the medicament preferably includes a physiologic carrier selected from a commercially available petrolatum based ointment or U.S.P. cold cream.

BRIEF DESCRIPTION OF THE DRAWINGS

Reference to the following detailed description may help to better explain the invention in conjunction with the drawings which.

DETAILED DESCRIPTION OF THE INVENTION

Figure 1:
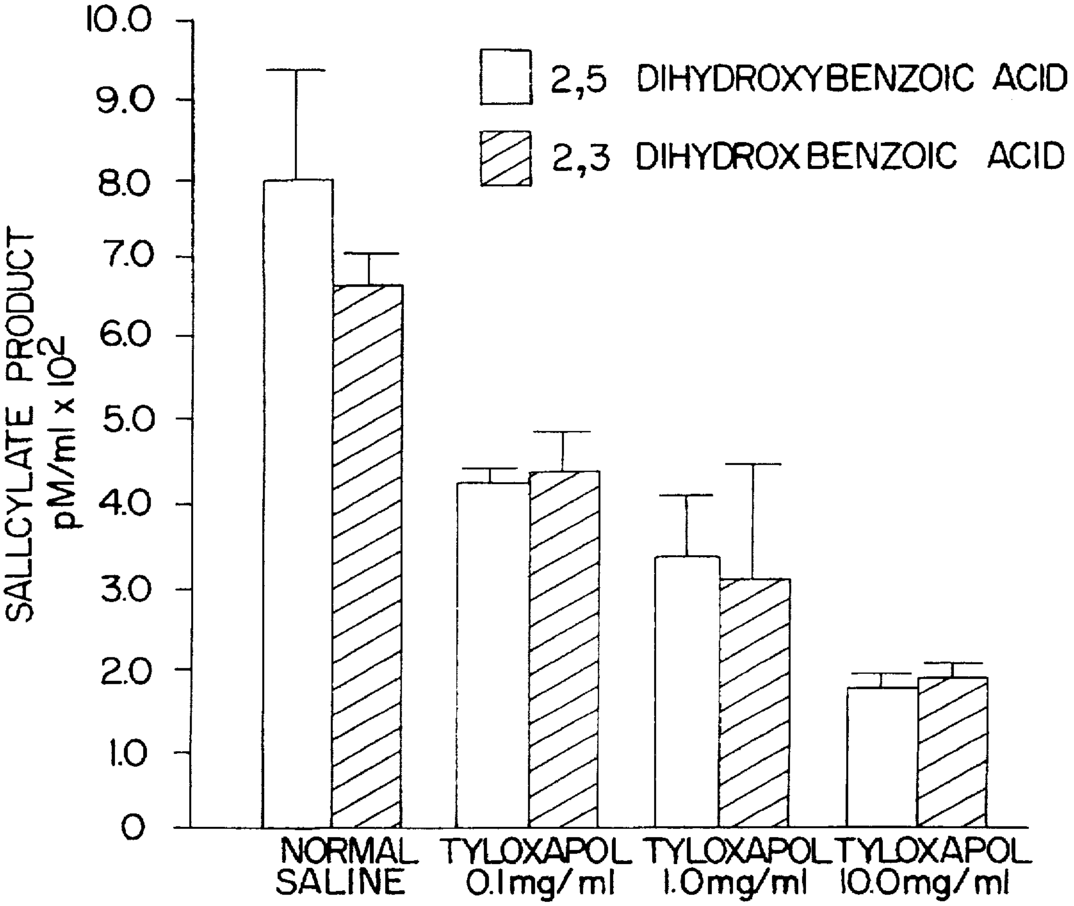
FIG. 1 shows a graph of the inhibitory effect of tyloxapol on °OH generation by the Fenton reaction, as measured by hydroxylation of salicylate.

Alkylaryl polyether alcohol polymers can in general be synthesized by condensing alkylaryl alcohols with formaldehyde, as described in U.S. Pat. No. 2,454,541, the disclosure of which is incorporated herein by reference. The present invention provides a medicament for the inhibition of injurious effects of partially reduced $O_2$ species in chemical and biologic systems comprising as a treatment an effective amount of alkylaryl polyether alcohol polymer of the formula:

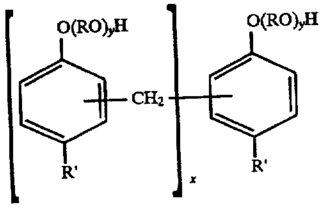

where R=ethylene, R'=$C_4$ to $C_{14}$ straight or branched alkyl, x is greater than 1, and y=2 to 18, effective to inhibit oxidant chemical reactions caused by the oxidant species in the mammal, thereby treating the mammalian disease entities. All alkylaryl polyether alcohol polymers disclosed in this patent should work in the present invention. Several specific alkylaryl polyether alcohol polymers can be synthesized by methods previously described (J. W. Cornforth, et al. "Antituberculous effect of certain surface-active polyoxyethylene ethers in mice". *Nature* (1951) 168:150–153). The prototype compound of this class, tyloxapol, can be conveniently purchased in pharmacologically acceptable purity from Nycomed, Inc., 33 Riverside Ave., Rensselaer, N.Y. 12144.

Treatment of patients for inhibition of the activation of transcription factor NF-κB and production of the cytokines TNF-α, IL-1β, IL-6, IL-8 and the growth factor GM-CSF with alkylaryl polyether alcohol polymers, particularly tyloxapol, is essentially the same as the administration described in U.S. Pat. No. 5,474,760 and U.S. Ser. No. 08/039,732, now abandoned. More specifically, for treatment of mammalian respiratory conditions related to an overproduction of partially reduced $O_2$ species, and for inhibition of the activation of transcription factor NF-κB and production of the cytokines TNF-α, IL-1β, IL-6, IL-8 and the growth factor GM-CSF, the alkylaryl polyether alcohol polymer is dissolved in sterile 0.9% NaCl for injection, and the pH is adjusted to approximately 7.0 by addition of NaOH or HCl. A nonpolymeric alkyl or aryl alcohol such as cetyl alcohol (hexadecanol) may be added equivalent to 1 to 1.5 times the weight of tyloxapol to increase the effectiveness of the mixture in protection against oxidant injury.

This mixture is then administered to the lung by direct instillation into the respiratory system. The mixture may also be administered by aerosolization using a clinically available positive pressure driven nebulizer that produces respirable particles of less than 5 microns mass median diameter.

As an example, a 0.125 to 0.5% solution of tyloxapol is made in sterile 0.9% NaCl and double glass distilled deionized water to make it isotonic with respect to respiratory secretions. The pH is adjusted to approximately 7.0 to prevent bronchospasm from extremes of acidity or alkalinity. This mixture is sterilized by vacuum filtration through a 0.22 micron Millipore filter and 3.3 ml each is packaged into 5 ml unit dose glass vials with rubber stoppers fastened with aluminum crimp-on "flip-tear" seals. To provide additional sterilization of product, unit dose vials are terminally autoclaved 12–14 minutes at 125° C. A 0.5% concentration of glycerol may be optionally added to the above mixture to stabilize droplet size during aerosolization.

To enhance the effectiveness of the therapy, a treatment effective amount of a commonly available anti-inflammatory steroids, such as methylprednisolone (1–5 mg), triamcinolone (1–5 mg), beclomethasone dipropionate (1–4 mg), flunisolide (200–400 μg) or dexamethasone (200–400 μg, either as dexamethasone or its water soluble congener dexamethasone sodium phosphate) may be added to the formulation. The amount of tyloxapol to steroid to be effective will vary depending upon which steroid is used. For example, a ratio of 5 mg. tyloxapol to 25 mg. of methylprednisolone, 5 mg of tyloxapol to 25 mg. of triamcinolone, 6 mg. of tyloxapol to 25 mg. of beclomethasone dipropionate, 125 mg. of tyloxapol to 250 mg. of flunisolide, or 125 mg. tyloxapol to 250 mg. of dexamethasone, either as dexamethasone are preferred. Combining an alkylaryl polyether alcohol polymer and an anti-inflammatory steroid provides a means for reducing steroid resistance in asthma and other diseases, thereby enhancing steroid effectiveness. This is accomplished by blocking, with addition of the alkylaryl polyether alcohol polymer, activation of the transcription factor NF-κB, thereby preventing binding and thereby mutual repression of the steroids receptor complex by active NF-κB present in the cytoplasm. An additional advantage of the combined formulation is that alkylaryl polyether alcohol polymers, as surface active agents, will aid in the solubilization of water-insoluble anti-inflammatory steroids such as triamcinolone, beclomethasone dipropionate, flunisolide or dexamethasone, thereby promoting their effective distribution to the airway.

For administration of treatment effective doses to the lungs and bronchial airways, 3 ml of sterile tyloxapol solution is inhaled as an aerosol every 4 to 12 hours using a clinically available positive pressure driven nebulizer (Acorn or deVilbiss). Alternately, the mixture can be nebulized into the respiratory delivery circuit of a mechanical ventilatory. A beta sympathetic agonist bronchodilator (such as 1.25 to 2.5 mg of albuterol) can be mixed with the tyloxapol solution and nebulized concomitantly to prevent any transient bronchospasm that might occur from the tyloxapol or tyloxapol-steroid solution itself. A quaternary ammonium derivative of atropine such as ipratoprium (500 μg) or glycopyrrolate (200–1,000 μg) can also be added to the tyloxapol solution as a bronchodilator for the same purpose.

For administration of treatment effective doses to the nasal airway, the sterile tyloxapol solution or tyloxapol solution containing the above anti-inflammatory steroid is placed in a commercially available 10 ml squeeze bottle or similar device that generates a fine mist. For relief of nasal rhinitis, rhinosinusitis or other inflammation, 1 to 4 sprays from this dispense is inhaled into each nostril 2 to 4 times a day.

For treatment of cutaneous inflammatory disorders such as solar burn, psoriasis or other dermatoses, a 0.5 to 5% mixture (w/w) is made with an alkylaryl polyether alcohol such as tyloxapol, or tyloxapol and an anti-inflammatory steroid such as hydrocortisone, triamcinolone or flunisolide, in a commercially available petrolatum based ointment such as Aquaphor (Beiersdord, Inc., Norwalk, Conn.), white petrolatum or U.S.P. cold cream as the base vehicle. This mixture is rubbed lightly onto the affected skin area 3 to 4 times daily.

In order to facilitate a further understanding of the invention, the following examples primarily illustrate certain more specific details thereof.

Example I demonstrates the potent activity of alkylaryl polyether alcohol polymers as °OH scavengers in chemical systems. Example II demonstrates the therapeutic benefit of using alkylaryl polyether alcohol polymers to prevent mammalian lung injury from exposure to 100% oxygen. Example III demonstrates the potent activity of alkylaryl polyether alcohol polymers as scavengers of HOCl in chemical systems. Example IV demonstrates inhibition of activation of the transcription factor NF-κB. Example V demonstrates suppression of cytokine and GM-CSF production.

EXAMPLE I

Inhibition of Oxidants Generated by the Fenton Reaction

The first chemical system used to test the antioxidant activity of alkylaryl polyether alcohol polymers employed salicylate as the target molecule of oxidants. The hydroxyl radical reacts with salicylic acid (2 hydroxybenzoic acid) to produce two dihydroxybenzoic acid products, 2,3- and 2,5-dihydroxybenzoic acid. These hydroxylated products provide evidence of °OH generation (R. A. Floyd et al. *Journal of Biochemical and Biophysical Methods* (1984) 10:221–235; R. A. Floyd et al. *Journal of Free Radicals in Biology & Medicine* (1986) 2:13–18).

The detection of 2,3- and 2,5-dihydroxybenzoic acid was performed using high performance liquid chromatography with electrochemical detection. Suspensions of 10 μM $FeCl_3$, 1 mM $H_2O_2$, 1.0 mM ascorbate and 10.0 μM salicylic acid were employed to generate and detect °OH. Either 1.0 ml of normal saline or tyloxapol (final concentrations of 0.0 to 10 mg/ml) were added. The reaction mixtures were incubated at 45° C. for 30 min and centrifuged at 1200 g for 10 min. Supernatant was centrifuged (Beckman Microfuge E) through a 0.22 μM microfuge tube filter (PGC Scientific No. 352-118) at 15,000 g.

A 100 μL sample of the eluate was injected onto a C18 RP HPLC column (250×4.7 mm, Beckman No. 235329). Hydroxylated products of salicylate were quantified with a Coulochem electrochemical detector (ESA model 5100 A) with the detector set at a reducing potential of −0.40 VDC. The guard cell (used as a screen) was set at an oxidizing potential of +0.40 VDC. Measurements were done in duplicate. FIG. 1 shows that the addition of tyloxapol to the reaction mixture inhibited °OH generation in a concentration dependent manner.

The second chemical system used to test the antioxidant activity of alkylaryl polyether alcohol polymers employed 2-deoxyribose as the target molecule of oxidants. This pentose sugar reacts with oxidants to yield a mixture of products. On heating with thiobarbituric acid (TBA) at low pH, these products form a pink chromophore that can be measured by its absorbance at 532 nm (B. Halliwell and J. M. C. Gutteridge. *Methods in Enzymology* (1990) 186:1–85).

The chemical system employed to generate oxidants was a reaction mixture containing 10.0 μM $FeCl_3$, 1.0 mM ascorbate, 1.0 mM $H_2O_2$ and 1.0 mM deoxyribose in Hanks Balanced Salt Solution. This system is useful for measuring site-specific °OH generation on biologic molecules, as described by Halliwell and Gutteridge in the reference immediately above. Either 0.1 ml of normal saline or tyloxapol (final concentrations of 0.0 to 10.0 mg/mg) were added.

Figure 2:
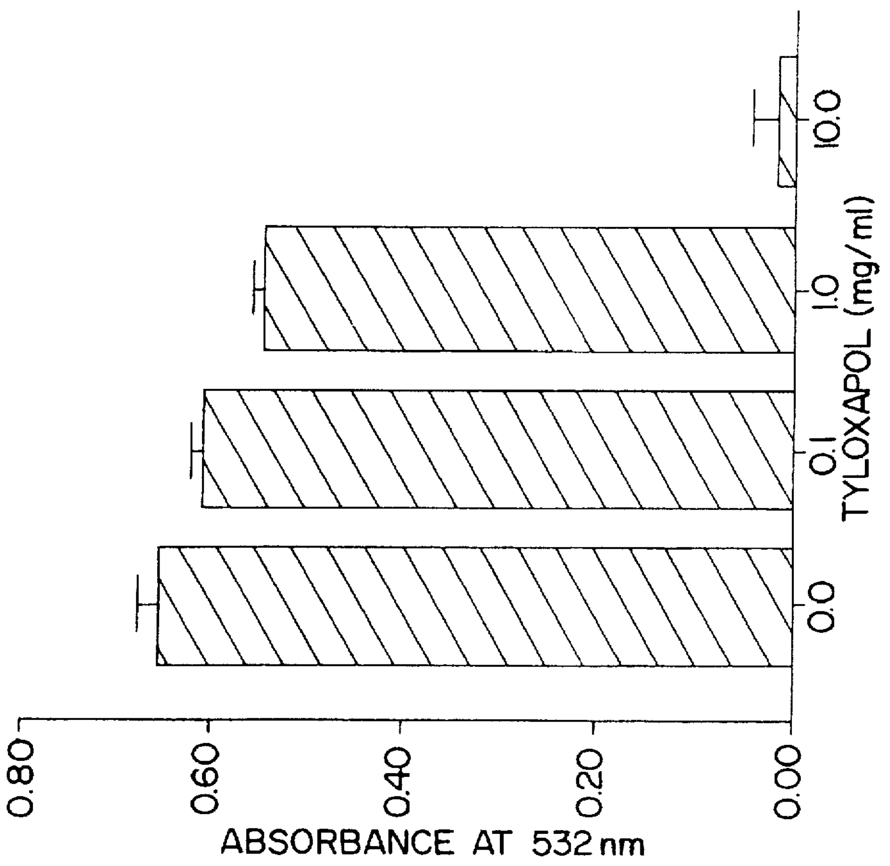
FIG. 2 shows a graph of the inhibitory effect of tyloxapol on °OH generation by the Fenton reaction, as measured by oxidation of the sugar, 2-deoxyribose.

The reaction mixtures were incubated at 45° C. for 30 min and centrifuged at 1200 g for 10 min. One ml of both 1.0% (w/v) TBA and 2.8% (w/v) trichloroacetic acid were added to 1.0 ml of supernatant, heated at 100° C. for 10 min, cooled in ice, and the chromophore determined in triplicate by its absorbance at 532 nm. FIG. 2 shows that the addition of 10 mg/ml tyloxapol to the reaction mixture causes marked inhibition of the oxidation of deoxyribose, as measured by absorbance of the oxidant reaction produced at 532 nm.

The third system used to test the antioxidant activity of alkylaryl polyether alcohol polymers employed asbestos as the source of iron for oxidant generation and 2-deoxyribose as the target molecule of oxidants. The generation of oxidants by asbestos has been described previously (A. J. Ghio et al. *American Journal of Physiology* (*Lung Cellular and Molecular Physiology 7*) (1992) 263:L511–L518). The reaction mixture, in a total volume of 2.0 ml phosphate-buffered saline (PBS) contained the following reagents: 1.0 mM deoxyribose, 1.0 mM $H_2O_2$, 1.0 mM ascorbate, and 110 mg/ml crocidolite asbestos. The mixture was incubated at 37° C. for 1 hour with agitation and then centrifuged at 1,200 g for 10 min.

Oxidant generation was assessed by measuring TBA reactive products of deoxyribose as detailed in the paragraph above. Measurements were done in triplicate. TABLE I below shows that the addition of tyloxapol inhibited in a concentration dependent manner the generation of oxidants by asbestos, as measured by absorbance of the oxidant reaction product at 532 nm.

TABLE I

Effect of Tyloxapol on Oxidant Generation of Asbestos

| | Absorbance at 532 nm |
|---|---|
| Tyloxapol 0.0 mg/ml | 0.93 ± 0.02 |
| Tyloxapol 0.1 mg/ml | 0.89 ± 0.04 |
| Tyloxapol 1.0 mg/ml | 0.75 ± 0.01 |
| Tyloxapol 10.0 mg/ml | 0.53 ± 0.04 |

EXAMPLE II

Protection from Mammalian Lung Injury by 100% Oxygen

To determine if alkylaryl polyether alcohol polymers could protect against oxidant injury to intact biologic systems, this treatment was studied in a well established model of oxygen toxicity to the lung (J. F. Turrens, et al. *Journal of Clinical Investigation* (1984) 73:87–95). Sixty-day old male Sprague-Dawley rats (Charles River, Inc., Wilmington, Mass.) were tracheally instilled with 0.5 ml of either normal saline, tyloxapol (6.0 mg) or tyloxapol (6.0 mg) and cetyl alcohol (hexadecanol, 11.0 mg). These rats (n=10 in each treatment group) were then exposed to either air or 100% oxygen in plexiglass chambers at a flow rate of 10 liters/min.

Oxygen percentage was monitored by a polarographic electrode and maintained continuously above 98%. Temperature was maintained between 20 and 22° C. Survival times were determined by checking animals every 4 hours. Separate groups of rats treated similarly (n=10 in each treatment group) were exposed to 100% oxygen for 61 hours, and then were euthanized with 100 mg/kg intraperitoneal pentobarbital. Pleural fluid volume was measured by aspirating pleural fluid from the chest cavity through a small incision in the diaphragm. Lung wet/dry weight ratios were calculated from the left lung after drying the tissue for 96 hours at 60° C. Survival data is shown in TABLE II below.

Rats receiving intratracheal tyloxapol had markedly improved survival compared to placebo control animals instilled with saline. The protective effect of tyloxapol was further enhanced by combining it with cetyl alcohol.

TABLE II

Effect of Tyloxapol on Oxygen Toxicity in Rats

| | Percent Survival | | |
|---|---|---|---|
| Hours | Saline | Tyloxapol | Tyloxapol/ Cetyl Alcohol |
| 0 | 100 | 100 | 1 |
| 58 | 100 | 100 | 100 |
| 62 | 83 | 100 | 100 |
| 66 | 42 | 100 | 100 |
| 70 | 17 | 75 | 100 |
| 72 | 17 | 75 | 100 |
| 76 | 8 | 58 | 100 |
| 80 | 8 | 58 | 100 |
| 84 | 8 | 58 | 100 |
| 88 | 8 | 58 | 100 |
| 92 | 0 | 58 | 100 |
| 96 | 0 | 58 | 100 |

Figure 3:
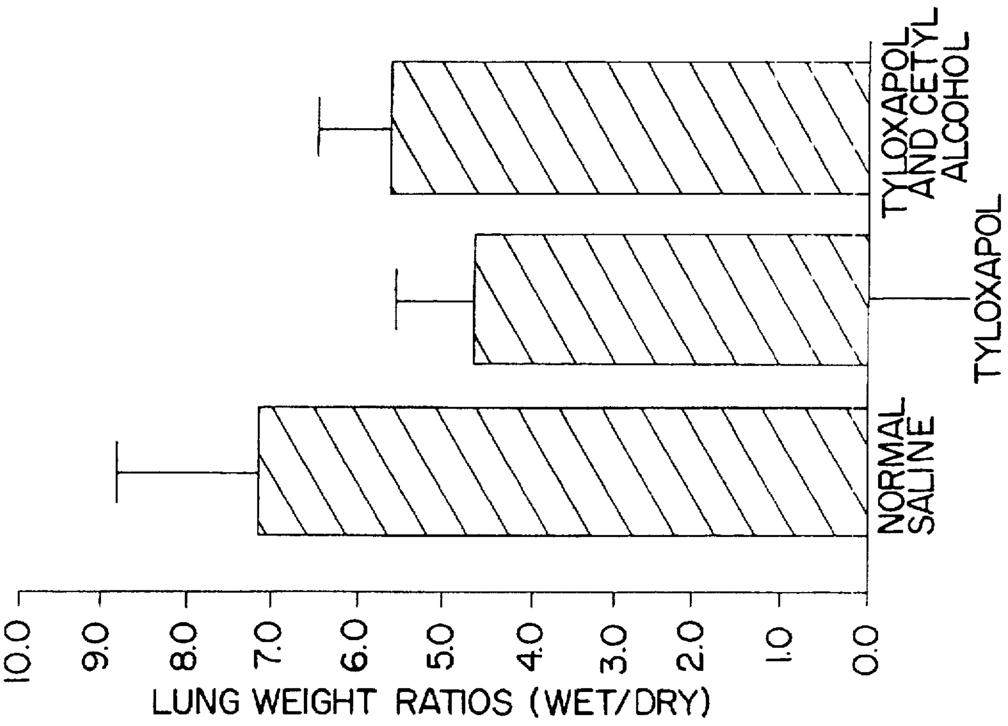
FIG. 3 shows lung wet/dry weight ratios in rats exposed to 100% oxygen and treated with normal saline, tyloxapol, and tyloxapol plus cetyl alcohol.
Figure 4:
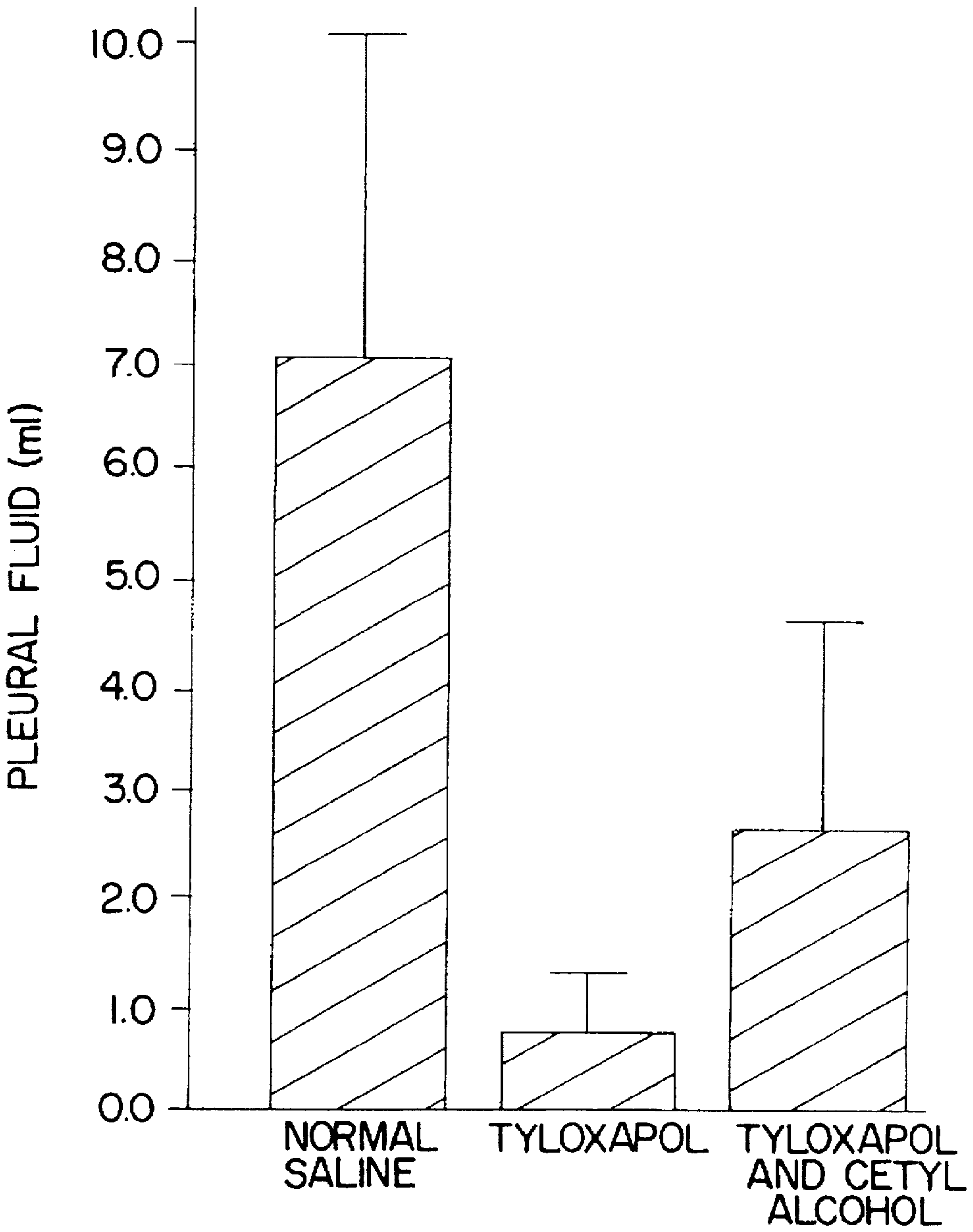
FIG. 4 shows pleural fluid accumulation in rats exposed to 100% oxygen and treated with normal saline, tyloxapol, and tyloxapol plus cetyl alcohol.

Lung wet/dry weight ratios were substantially lower in rats treated with tyloxapol or tyloxapol and cetyl alcohol (FIG. 3), demonstrating that tyloxapol or the combination of tyloxapol and cetyl alcohol protect against edema formation from oxidant injury. Rats treated with tyloxapol or the combination of tyloxapol and cetyl alcohol also had less pleural fluid accumulation than saline treated controls (FIG. 4).

These results demonstrate the ability of alkylaryl polyether alcohol polymers such as tyloxapol to protect against oxidant tissue injury. The survival studies (TABLE II) further demonstrate that the protective effect of the medicament is enhanced by combining it with alcohols such as cetyl alcohol.

EXAMPLE III

Scavenging of HOCl

The activity of tyloxapol to scavenge $OCl^{-1}$ was tested by studying its ability to prevent $OCl^{-1}$ mediated oxidant conversion of diethanolamine to its corresponding stable chloramine ("Determination of HOCl Production by Myeloperoxidase", Robert A. Greenwald, editor, *Handbook of Methods for Oxygen Radical Research*, CRC Press, Boca Raton, Fla. (1987), page 300).

The reaction mixture comprised 0.9 ml of 10.0 mM diethanolamine in 0.1N sodium acetate buffer, pH 4.5. To this was added either 100 μL of 0.1M NaCl or tyloxapol in 0.1M NaCl, and the baseline absorbance was read at 280 nm. NaOCl was added to a final concentration of 10 mM.

The reaction mixture was incubated 15 minutes, and the absorbance was measured at 280 nm. The difference in $A_{280}$ before and after addition of NaOCl was used as a measure of concentration of the stable chloramine. Experiments were performed in triplicate. Results are summarized in Table III below:

TABLE III

| Microliters of Tyloxapol (10 mg/ml) | Absorbance (mean ± SD) |
| --- | --- |
| 0 | 0.505 ± 0.002 |
| 25 | 0.468 ± 0.008 |
| 50 | 0.444 ± 0.023 |
| 75 | 0.377 ± 0.010 |
| 100 | 0.319 ± 0.025 |

To demonstrate that tyloxapol is also an effective scavenger of HOCl in vivo, the ability of tyloxapol to protect against lung injury from HOCl was studied in 60-day old male Sprague-Dawley rats (n=6 per treatment group) weighing 250–300 g (Charles River Breeding Labs, Wilmington, Mass.). After anesthesia with halothane (2–5%) rats were injected intratracheally with either 0.3 ml of 2.0 mM NaOCl in normal saline (buffered to pH 6.0), or with normal saline alone. The rats were allowed to recover, and one hour later were dosed intratracheally with either 6.0 mg tyloxapol in normal saline or with normal saline. Twenty-four hours after NaOCl instillation, all rats were euthanized with sodium pentobarbital. The tracheas were cannulated and lungs were lavaged with normal saline (35 ml/kg body weight). After staining of the lavage fluid with a modified Wright's stain (Diff-Quick stain, ASP, McGraw Park, Ill.), the cell differentials were determined on 500 cells/sample. Values were expressed as the percentage of total cells recovered. Lavage protein was measured using the Bio-Rad method for total protein determination as modified for use on the centrifugal analyzer.

Figure 5A:
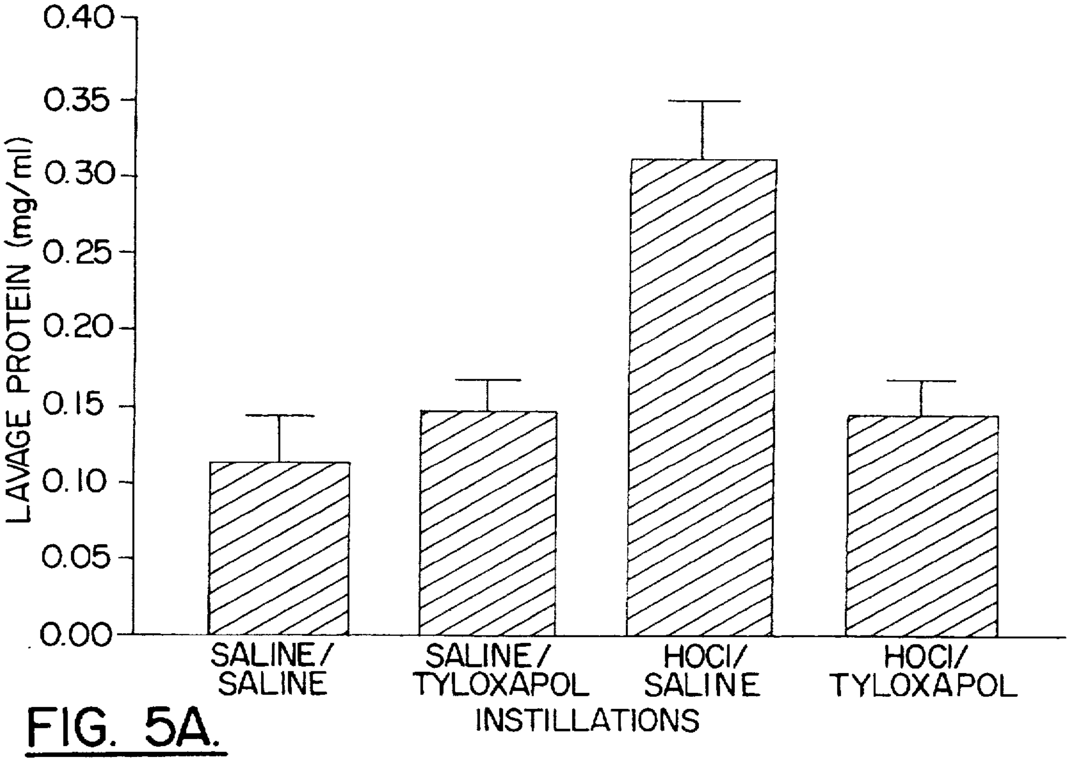
FIG. 5A shows the effect of tyloxapol on HOCl-mediated lung injury in rats as shown by an increase in protein concentration.
Figure 5B:
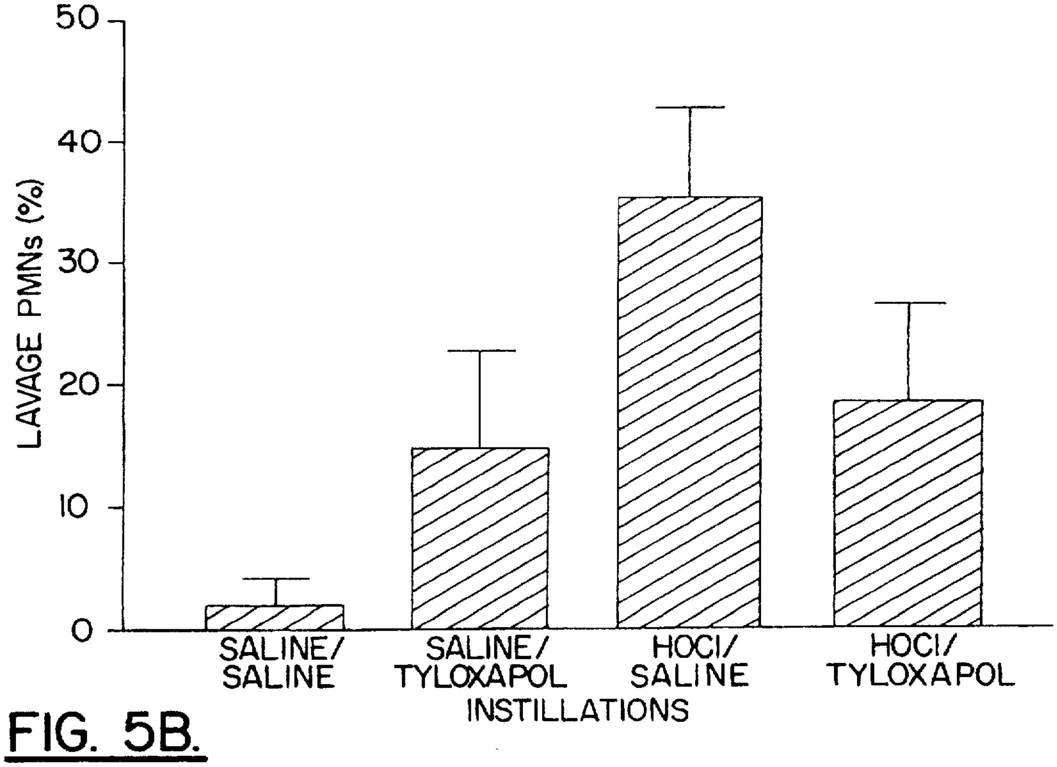
FIG. 5B shows the effect of tyloxapol on HOCl-mediated lung injury in rats as shown by an increase in % neutrophils.

Intratracheal instillation of NaOCl caused acute lung injury as demonstrated by a marked increase in protein concentration (FIG. 5A) and % neutrophils (% PMNs) (FIG. 5B) in lung lavage fluid. Post exposure treatment with tyloxapol significantly reduced lavage protein concentration ($p<0.001$) and % PMNs ($p<0.01$), demonstrating that tyloxapol also protects against HOCl-mediated cytotoxicity in vivo.

Thus, tyloxapol is a potent inhibitor of the oxidant activity of HOCl, and should be useful in preventing HOCl mediated oxidant injury of the airway. Administration of tyloxapol by tracheal instillation to patients with neutrophil-mediated airways diseases such as cystic fibrosis and chronic bronchitis should inhibit HOCl produced in these patients and therefore protect them from oxidant injury. The result should be even better if some cetyl alcohol is admixed with the tyloxapol; preferably, the cetyl alcohol is added in 1 to 1.5 times the weight of the tyloxapol.

Preparation of samples for administration to the patient should be the same as described above, most preferably inhalation of 3 ml to a 0.125 to 0.5% solution of tyloxapol by jet aerosol every 4 to 12 hours.

- EXAMPLE IV

Inhibition of the Activation of Transcription Factor NF-κB by Tyloxapol

Control of genetic expression of cell proteins is controlled by proteins called transcription factors which bind to regulatory DNA sequences and influence production of the protein product of the regulated gene. An important transcription factor for inflammation is NF-κB, which promotes transcription of the messenger RNA for pro-inflammatory cytokines and growth factors.

To determine if tyloxapol inhibits activation of the transcription factor NF-κB, tyloxapol was tested in electrophoretic mobility gel shift assays performed on cultured A549 human lung epithelial cells. A549 human pulmonary epithelial cells were cultured in Ham's F-12 medium supplemented with 10% heat-inactivated fetal calf serum, L-glutamine (2 mM), penicillin (100 U/ml), streptomycin (100 μg/ml) and amphotericin B (250 μg/ml). Confluent cells were stimulated with 10 U/ml IL-1β or 100 μM $H_2O_2$. In some cultures 100 μg/ml tyloxapol was added at the same time as the stimulators. After 2 hours of incubation, nuclear extracts were isolated as described by Dignam et al. (J. D. Dignam, R. M. Lebovita, and R. G. Roeder. "Accurate transcription initiation by RNA polymerase II in a soluble extract from isolated mammalian nuclei" *Nucleic Acid Research* (1983) 11:1475–1489), with minor modifications (C. V. Gunther and B. J. Graves "Identification of ETS domain proteins in murine T lymphocytes that interact with the Moloney murine leukemia virus enhancer" *Molecular and Cellular Biology* (1994) 14:7569–7580). In brief, after removal of the supernatant, cells were scraped gently in 20–30 ml of PBS containing 1 mM phenylmethylsulfonyl fluoride (PMSF) and 1 mM dithiothreitol (DTT). The cell suspension were centrifuged and the pellets were resuspended and incubated for 15 min in 1 ml buffer A containing 10 mM HEPES, 1.5 mM $MgCl_2$, 10 mM KCl, 1 mM PMSF, 1 mM DTT, 10 mM β-glycerolphophate, 2.5 mM benzamidine, 1 mM NaF, 1 mM $NaVO_4$, 1 mg/ml leupeptin and 1 mg/ml pepstatin A, then were sheared by 5 times passage of the suspensions through a 25 G needle. After centrifugation, the pellets were suspended and stirred for 30 min in buffer C containing 25% vol/vol glycerol, 0.25M NaCl, 1.5 mM $MgCl_2$, 0.2 mM ethylenediamine tetraacetic acid (EDTA), 1 mM PMSF, 1 mM DTT, 10 mM β-glycerolphophate, 2.5 mM benzamidine, 1 mM NaF, 1 mM $NaVO_4$, 1 mg/ml leupeptin and 1 mg/ml pepstatin A. After centrifugation, nuclear extracts were obtained by dialysis of the supernatants in buffer D containing 20 mM HEPES, 20% vol/vol glycerol, 100 mM KCl, 0.2 mM EDTA, 1 mM PMSF and 1 mM DTT. Utilizing the wild type consensus sequences for AP-1 (W. Lee, P. Mitchell and R. Tijan "Purified transcription factor AP-1 interacts with TPA-inducible enhancer elements" *Cell* (1987) 49:742–752) and NF-κB (R. Sen and D. Baltimore. "Multiple nuclear factors interact with the immunoglobulin enhancer sequences" *Cell* (1986) 46:705–716) loci, the following oligonucleotides were synthesized (binding sites underlined):

AP-1: 5'-TTCCGGC<u>TGACTCA</u>TCAAGCG-3' (SEQ ID NO:1)

3'-AAGGCCGACTGAGTAGTTCGC-5' (SEQ ID NO:2)

NF-κB: 5'-AGTTGAG<u>GGGACTTTCC</u>CAGGC-3' (SEQ ID NO:3)

3'-TCAACTCCCCTGAAAGGGTCCG-5' (SEQ ID NO:4)

The oligonucleotides were purified by denaturing polyacrylamide gel electrophoresis followed by passage over Sep-Pak C18 columns. Each complementary strand was end-labeled by phosphorylation with [$Y^{32}P$]-ATP and T4 polynucleotide kinase. Double-stranded DNA probes were generated by annealing the complementary end-labeled oligonucleotide strands, boiling for 3 min and slow-cooling to room temperature in a water bath. Unincorporated radionucleotides were removed by Sephadex G-25 column chromatography. Binding reactions were performed for 20 min on ice with 5–10 μg total protein in a 20 μL volume containing 300 ng bovine serum albumin (BSA), 1–2 μg poly(dI-dC), 50 mM DTT, 0.5 mM PMSF and 1–2×$10^4$ c.p.m. of $^{32}P$-labeled probes. In addition, a concentration of 6 mM $MgCl_2$ was used for AP-1 binding reactions. In selected samples a 100-fold molar excess of unlabeled DNA probe was included in the binding reaction in order to confirm the specificity of DNA-protein interactions. DNA-protein complexes were separated from unbound DNA probe on 4.5% polyacrylamide gels under high ionic strength conditions in 50 mM (hydroxymethyl) aminomethane (Tris), 0.4M glycine, 2 mM EDTA and 2.5% vol/vol glycerol, pH 8.5. Electrophoresis was carried out at 4° C. at a constant current of 20 mA. Gels were dried under vacuum and exposed to film at −70° C. for 6–24 hours with an intensifier screen.

Figure 6:
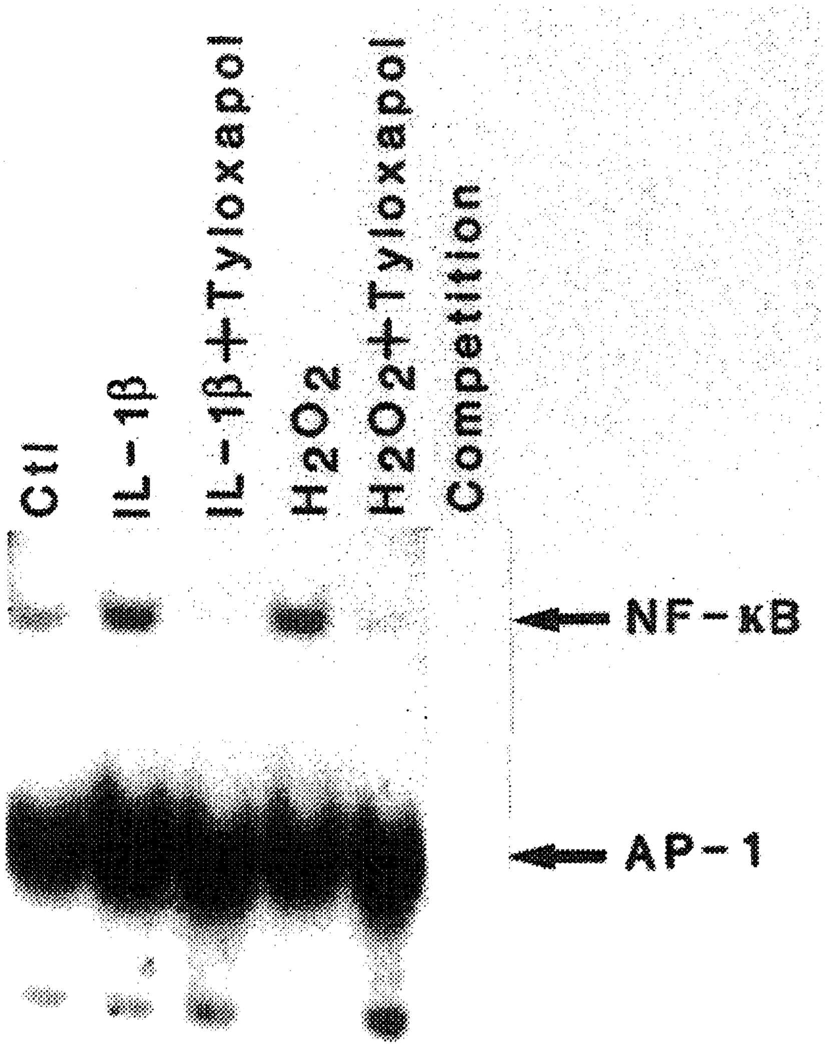
FIG. 6 shows activation of the transcription factor NF-κB by IL-1 and $H_2O_2$ and inhibition of this activation by tyloxapol.

As shown in FIG. 6, tyloxapol prevents IL-1β or $H_2O_2$ induced binding of NF-κB, but not AP-1, to nuclear extracts. Confluent A549 human pulmonary epithelial cells were incubated without (lane 1) or with 10 U/ml of IL-1β (lanes 2 and 3) or 100 μM $H_2O_2$ (lanes 4 and 5). Tyloxapol (100 ug/ml, lanes 3 and 5) was added at the same time as stimulators. After 3 hours of incubation, nuclear extracts were prepared. Aliquots of the extracts were incubated with $^{32}P$-labeled NF-κB- and AP-1-specific oligonucleotides and analyzed in electrophoretic mobility shift assays as detailed above. Position of the specific DNA-protein complexes are indicated by the arrowhead. One hundred-fold molar excess of the appropriate unlabeled DNA probe was included in the binding reactions for the samples shown in the competition lanes.

Thus, tyloxapol inhibits activation of the transcription factor NF-κB. This action is specific, since the activation of another important transcription factor, AP-1, was not affected. Blocking activation of NF-κB would carry the advantage of reducing cell production of pro-inflammatory cytokines and growth factors, thereby ameliorating inflammation in the tissue treated.

EXAMPLE V

Suppression of Cytokine Production by Tyloxapol

Inhibiting activation of the transcription factor NF-κB would be expected to reduce secretion of the pro-inflammatory cytokines influenced by NF-κB. As examples, cachexia and/or anorexia prominent in patients with severe cystic fibrosis lung disease is caused by an increased rate of TNF gene transcription and secretion by cystic fibrosis macrophages. (See K. D. Pfeffer, et al. "Expression and regulation of tumor necrosis factor in macrophages from cystic fibrosis patients". *American Journal of Respiratory, Cell and Molecular Biology.* (1993) 9:511–519). TNF is also an important mediator in the pathogenesis of asthma (R. J. Horwitz and W. W. Busse. "Inflammation and asthma". *Clinics in Chest Medicine* (1995) 16:585–602). Tyloxapol should ameliorate the adverse effects of TNF in cystic fibrosis and asthmatic pathophysiology when administered to cystic fibrosis or asthmatic patients because, as shown below, it is a potent suppressant of TNF secretion by monocyte-macrophage cell lines. By inhibiting TNF secretion, tyloxapol should also lessen the corticosteroid resistance in asthma caused in part by this cytokine (P. J. Barnes, et al. "Glucocorticoid resistance in asthma". *American Journal of Respiratory and Critical Care Medicine* (1995) 152:S125–S142). Also, IL-8 is a potent chemoattractant for polymorphonuclear neutrophils, and plays a prominent role in the pathogenesis of diverse diseases such as cystic fibrosis, chronic bronchitis, Adult Respiratory Distress Syndrome, and psoriasis (See, H. Nakamura, et al, "Neutrophil elastase in respiratory epithelial lining fluid of individuals with cystic fibrosis induces interleukin-8 gene expression in a human bronchial epithelial cell line". *Journal of Clinical Investigation* (1992) 89:1478–1484; N. G. McElvaney, et al. "Modulation of airway inflammation in cystic fibrosis". In vivo suppression of interleukin-8 levels on the respiratory epithelial surface by aerosolization of recombinant secretory leukoprotease inhibitor. *Journal of Clinical Investigation* (1992) 90:1296–1301; M. Baggiolini, et al. "Interleukin-8 and related chemotactic cytokines". In *Inflammation: Basic Principles and Clinical Correlates,* second edition. J. I. Gallin, I. M. Goldstein, and R. Snyderman, editors. Raven Press, Ltd., New York (1992) p. 247–263). By inhibiting IL-8 secretion, tyloxapol should ameliorate the influx of neutrophils into inflamed tissue in these diseases. Finally, GM-CSF is an important growth factor activating and lengthening the life-span of eosinophils in asthma (D. W. Golde and G. C. Baldwin. "Myeloid growth factors". In *Inflammation: Basic Principles and Clinical Correlates,* second edition. J. I. Gallin, I. M. Goldstein, and R. Snyderman, editors. Raven Press, Ltd., New York (1992) p. 291–301; R. J. Horwitz and W. W. Busse. "Inflammation and asthma". *Clinics in Chest Medicine* (1995) 16:583–602). By reducing GM-CSF secretion, tyloxapol should help reduce the eosinophilia and its consequences for the asthmatic airway.

To test the effect of tyloxapol on cytokine secretion, monocytes were prepared by centrifugal elutriation from leukopaks obtained from healthy human donors. Purified monocytes were suspended at 2×$10^6$ cells in RPMI-1640 supplemented with 100 U/ml penicillin, 100 μg/ml streptomycin, 2 mM L-glutamine, 1 mM sodium pyruvate, 1% MEM non-essential amino acids, 25 mM N-2-hydroxyethyl-ierazine-N'-ethane sulfonic acid (HEPES) and 196 Nutridoma (Boehringer Mannheim, Indianapolis, Ind.), and 5% pooled, heat-inactivated human AB serum (Pel-freeze, Brown Deer, Wis.).

One-half ml of this cell suspension was added to each well of a 48-well flat bottomed tissue culture plate. Test materials (diluted in complete medium at 4X the desired final concentration) were added in 250 μL volumes to each well. Control wells received 250 μL of either complete medium or 250 μL of IL-4 (diluted to 4X the desired final concentration of 50 μg/ml).

Tyloxapol was tested in triplicate at four concentrations in either the presence or absence of 100 ng/ml *Salmonella typhosa* lipopolysaccharide (LPS, 250 μL of 4X desired final concentration added) and incubated at 37° C. in humidified 5% $CO_2$ for 16 hours. At this time culture supernatants were aspirated off and the unattached cells and cell debris were removed by filtration. The release of TNF-α, IL-1β, IL-6 and IL-8 and the growth factor GM-CSF was determined in the cell-free supernatants using ELISA capture assays. The concentration of endotoxin in all buffers and tyloxapol was below the level of detection (25 pg/ml). Incubations of monocytes in concentrations of tyloxapol equal to or below 100 μg/ml were associated with no significant elevations in LDH concentration in the supernatant, supporting a lack of cytotoxicity by tyloxapol, and suggesting that the inhibition of cytokine secretion noted below was not due to an injurious detergent effect on monocytes.

Figure 7:
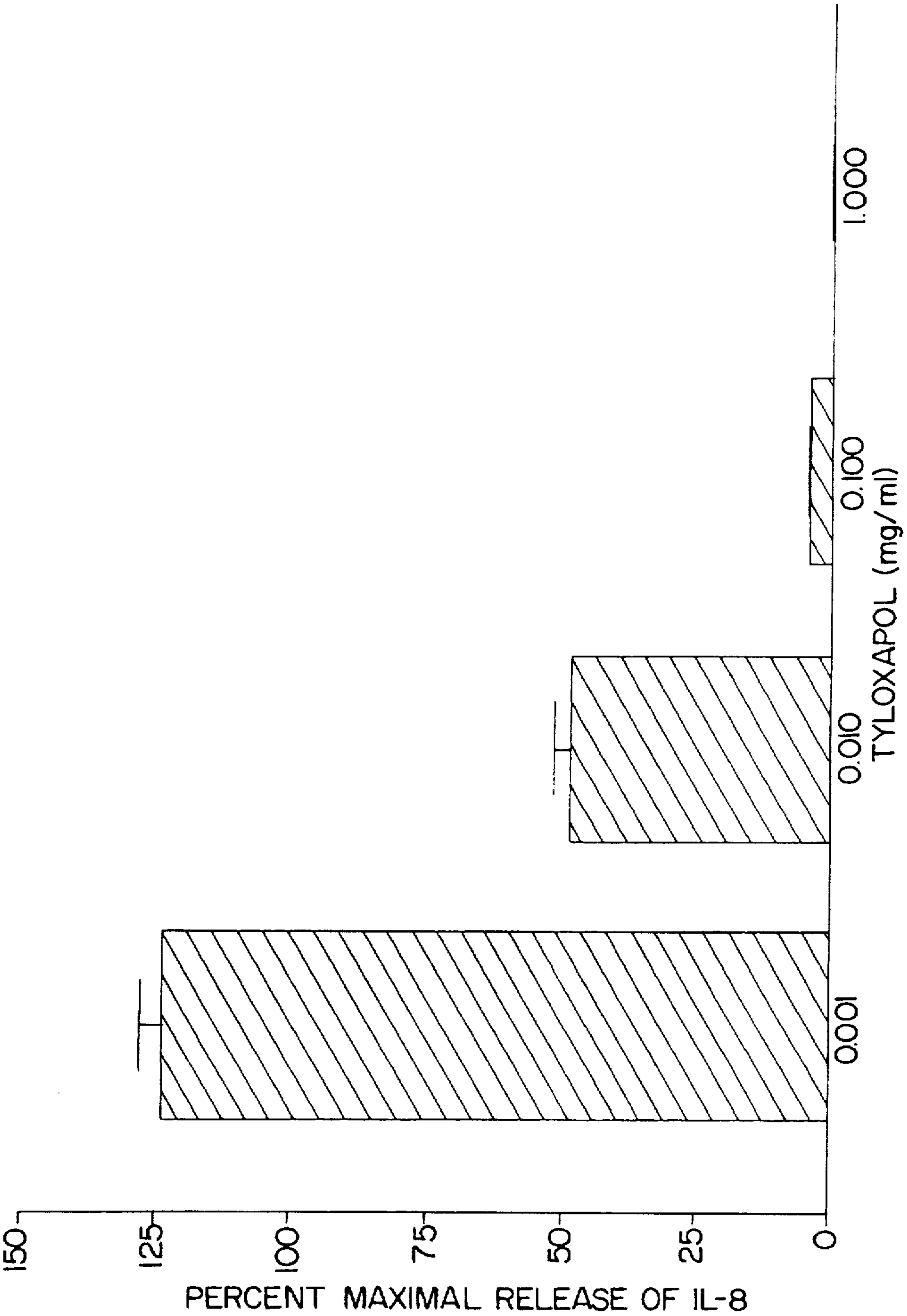
FIG. 7 shows baseline secretion of IL-8 by unstimulated human monocytes with and without tyloxapol treatment.
Figure 8A:
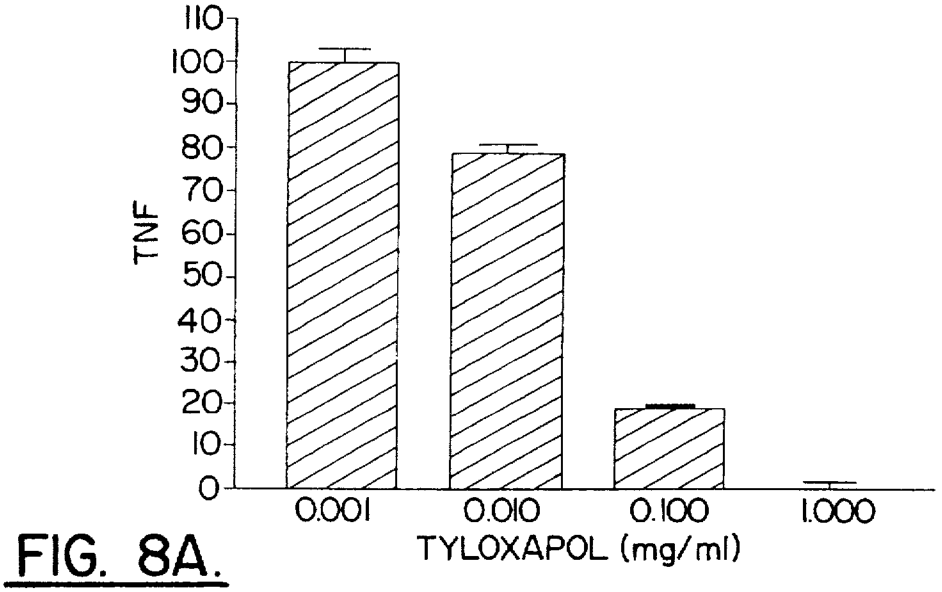
FIG. 8A shows human monocyte secretion of TNF-α with and without tyloxapol treatment.
Figure 8B:
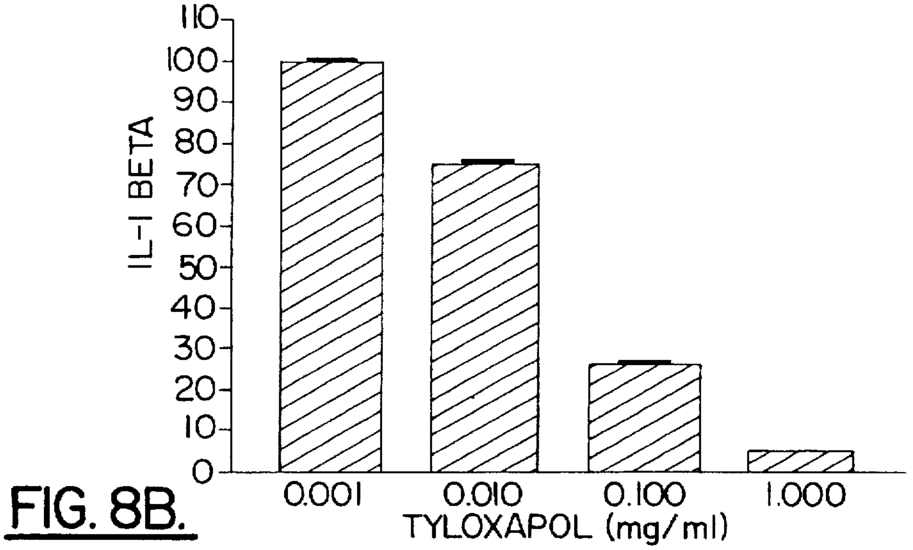
FIG. 8B shows human monocyte secretion of IL-1β with and without tyloxapol treatment.
Figure 8C:
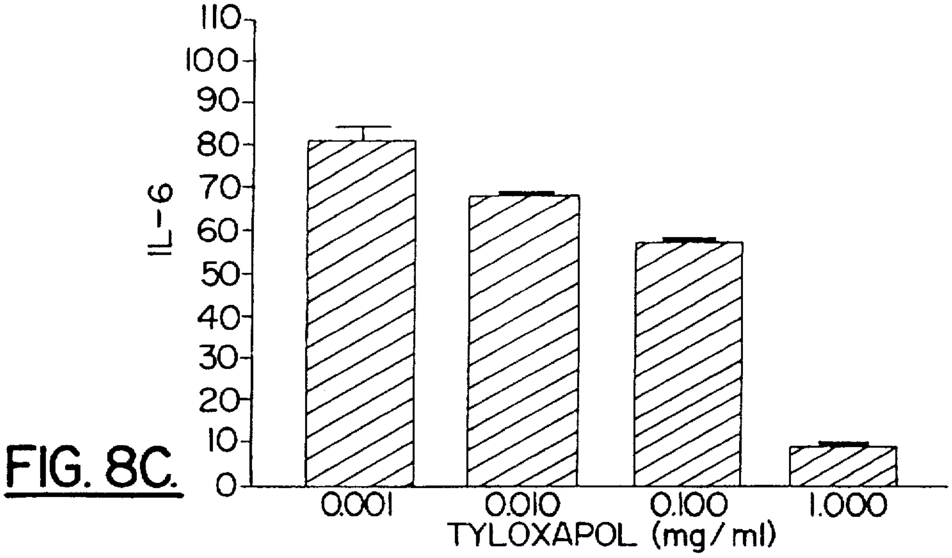
FIG. 8C shows human monocyte secretion of IL-6 with and without tyloxapol treatment.
Figure 8D:
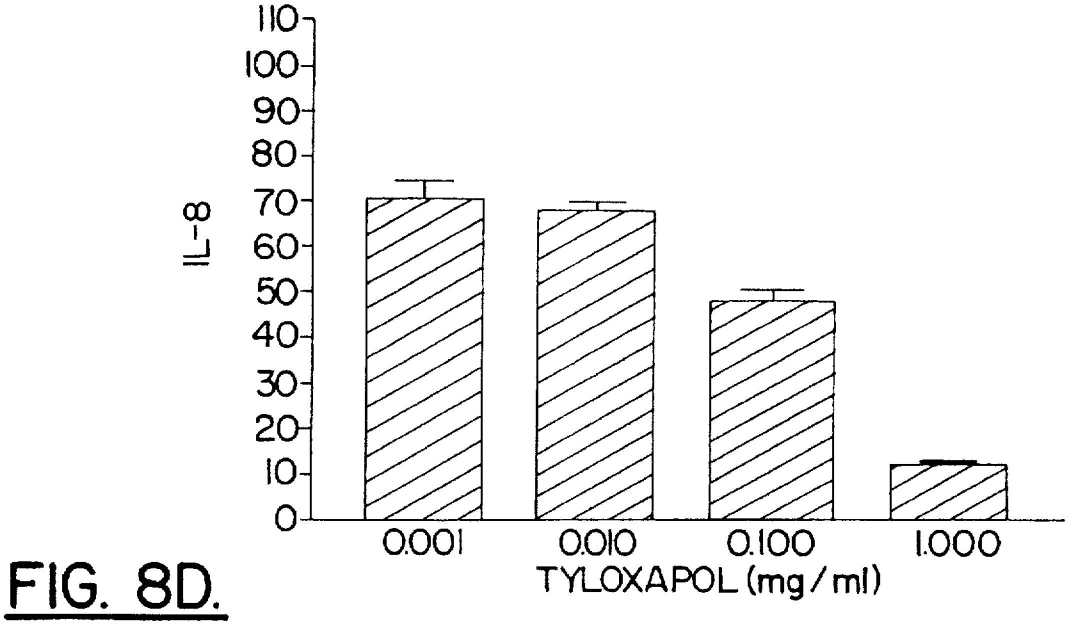
FIG. 8D shows human monocyte secretion of IL-8 with and without tyloxapol treatment.
Figure 8E:
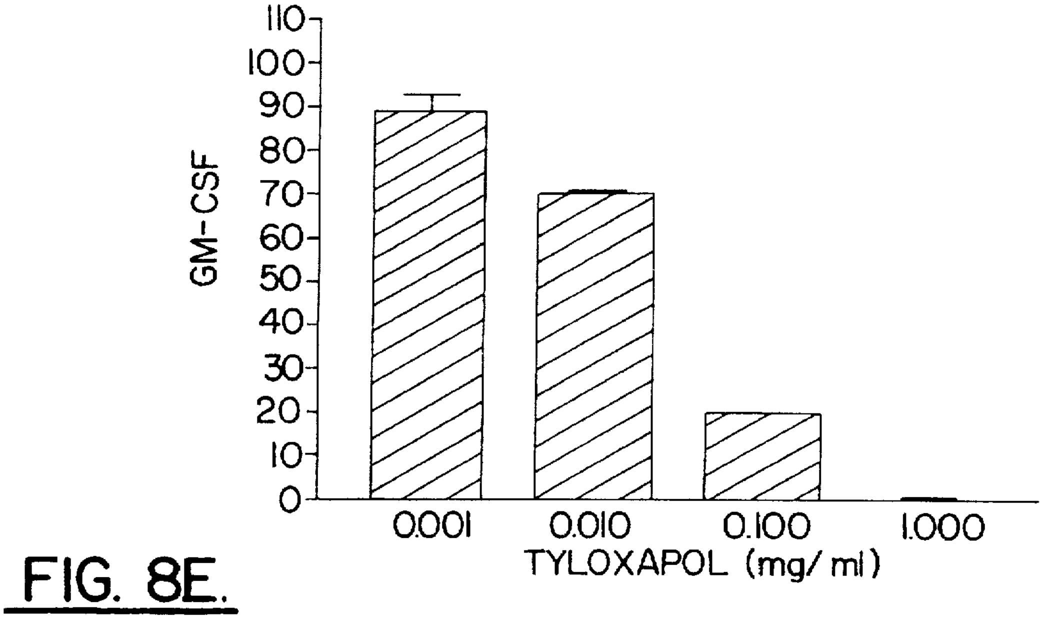
FIG. 8E shows human monocyte secretion of GM-CSF with and without tyloxapol treatment.

Tyloxapol had no effect on baseline release of any mediator except for IL-8, but significantly decreased secretion of IL-8 in unstimulated cells (FIG. 7). However, release of several mediators by LPS stimulated monocytes was significantly diminished at low concentrations of tyloxapol.

Secretion of TNF-α, IL-1β, IL-6, IL-8 and GM-CSF was significantly ($p<0.01$) decreased by tyloxapol in a dose-dependent manner (FIGS. 8A–8E), with effective concentrations for 50% inhibition ($EC_{50}$ ranging from 30–70 μg/ml (Table IV, below). However, tyloxapol did not change PAF release from LPS stimulated monocytes, providing additional evidence that the effect of tyloxapol was selective on cytokines influenced by NF-κB.

TABLE IV

Effective Concentrations of Tyloxapol for 50% Inhibition $EC_{50}$ of Monocyte Cytokine Release

| Cytokine | $EC_{50}$ (μg/ml) |
|---|---|
| TNF-α | 30 |
| IL-1β | 60 |
| IL-6 | 30 |
| IL-8 | 70 |

Thus, tyloxapol is a potent inhibitor of pro-inflammatory cytokine secretion, a result expected of a therapeutic agent that inhibits the transcription factor NF-κB. As such, tyloxapol would be expected to help ameliorate cachexia and/or anorexia from TNF, such as in patients with cystic fibrosis.

Aerosolized tyloxapol would also be expected to reduce airway injury of diseases of airway, such as cystic fibrosis, asthma and chronic bronchitis, and diffuse lung inflammation and injury, such as in Adult Respiratory Distress Syndrome, by inhibiting local production of the chemoattractant IL-8, TNF, IL-1, IL-6 and GM-CSF. Topical tyloxapol would be expected to ameliorate inflammatory diseases of the skin such as psoriasis and response to solar or thermal burn by reducing local production of the same cytokines. The result should be even better if the tyloxapol is mixed in a formulation with glucocorticoids, since by inhibiting NF-κB by a different mechanism than does the glucocorticoid-GR receptor complex, tyloxapol would reduce cytokine-induced-NF-κB related resistance to anti-inflammatory glucocorticoids, as discussed above. Reduction in steroid resistance would, in turn, potentiate the overall anti-inflammatory activity of glucocorticoids and enhance amelioration of inflammation of the body compartment treated. Tyloxapol should also work even better if admixed with some cetyl alcohol, added in 1 to 1.5 times the weight of tyloxapol. Preparation of the samples for administration to the patient should be the same as described above, most preferably inhalation of 3 ml of a 0.5% solution of tyloxapol, with or without admixed anti-inflammatory glucocorticoid by jet aerosol every 4 to 12 hours, or topical application of a 0/5 to 5% (w/w) application of tyloxapol, with or without admixing an anti-inflammatory glucocorticoid, in an acceptable ointment to the affected area.

The appended claims set forth various novel and useful features of the invention.

What is claimed is:

1. A method of inhibiting activation of nuclear transcription factor NF-κB in a mammal comprising administering to a mammal an effective amount of a compound of the formula:

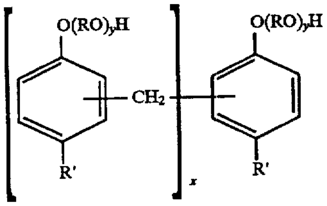

where R=ethylene, R'=$C_4$ to $C_{14}$ straight chain or branched alkyl, x is greater than 1, and y=8 to 18, whereby activation of nuclear transcription factor NF-κB is inhibited.

2. The method of inhibiting activation of nuclear transcription factor NF-κB according to claim 1 wherein said compound is tyloxapol.

3. The method of inhibiting activation of nuclear transcription factor NF-κB according to claim 1 wherein said administering comprises administering directly to the mammal's respiratory tract.

4. The method of inhibiting activation of nuclear transcription factor NF-κB according to claim 1 wherein said administering comprises administering said compound by aerosolization.

5. The method of inhibiting activation of nuclear transcription factor NF-κB according to claim 1 wherein said administering of said compound includes administering in a physiologically acceptable carrier.

6. The method of inhibiting activation of nuclear transcription factor NF-κB according to claim 1 wherein said administering further comprises administering a nonpolymeric alkyl or aryl alcohol.

7. The method of inhibiting activation of nuclear transcription factor NF-κB according to claim 6 wherein said alcohol is cetyl alcohol and said cetyl alcohol is added in an amount equivalent to 1 to 1.5 times the weight of said compound.

8. A method of inhibiting activation of nuclear transcription factor NF-κB, said method comprising administrating to a mammal an effective amount of a compound of the formula:

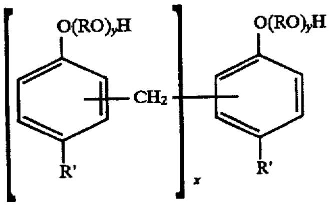

where R=ethylene, R'=C4 to $C_{14}$ straight chain or branched alkyl, x is greater than 1, and y=8 to 18, and an effective amount of an anti-inflammatory steroid to inhibit steroid resistance, whereby activation of nuclear transcription factor NF-κB is inhibited.

9. The method of inhibiting activation of nuclear transcription factor NF-κB according to claim 8 wherein said steroid is selected from the group consisting of methylprednisolone, triamcinolone, beclomethasone dipropionate, flunisolide and dexamethasone.

10. The method of inhibiting activation of nuclear transcription factor NF-κB according to claim 8 wherein said compound is tyloxapol.

11. The method of inhibiting activation of nuclear transcription factor NF-κB according to claim 8 wherein said administering comprises administering by aerosolization.

12. The method of inhibiting activation of nuclear transcription factor NF-κB according to claim 8 wherein said compound and said steroid are administered in a physiologically acceptable carrier.

13. The method of inhibiting activation of nuclear transcription factor NF-κB according to claim 8 wherein said compound is tyloxapol, said anti-inflammatory steroid is methylprednisolone, and the ratio of said tyloxapol to said methylprednisolone is 5 mg. to 25 mg.

14. The method of inhibiting activation of nuclear transcription factor NF-κB according to claim 8 wherein said compound is tyloxapol, said anti-inflammatory steroid is triamcinolone, and the ratio of said tyloxapol to said triamcinolone is 5 mg. to 25 mg.

15. The method of inhibiting activation of nuclear transcription factor NF-κB according to claim 8 wherein said compound is tyloxapol, said anti-inflammatory steroid is beclomethasone dipropionate, and the ratio of said tyloxapol to said beclomethasone dipropionate is 6 mg. to 25 mg.

16. The method of inhibiting activation of nuclear transcription factor NF-κB according to claim 8 wherein said compound is tyloxapol, said anti-inflammatory steroid is flunisolide, and the ratio of said tyloxapol to said flunisolide is 125 mg. to 250 mg.

17. The method of inhibiting activation of nuclear transcription factor NF-κB according to claim 8 wherein said compound is tyloxapol, said anti-inflammatory steroid is dexamethasone, and the ratio of said tyloxapol to said dexamethasone is 125 mg. to 250 mg.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( v ) FRAGMENT TYPE: linear ( x i ) SEQUENCE DESCRIPTION: SEQ ID NO:1:

TTCCGGCTGA CTCATCAAGC G 21

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( v ) FRAGMENT TYPE: linear ( x i ) SEQUENCE DESCRIPTION: SEQ ID NO:2:

AAGGCCGACT GAGTAGTTCG C 21

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single -continued ( D ) TOPOLOGY: linear ( v ) FRAGMENT TYPE: linear ( x i ) SEQUENCE DESCRIPTION: SEQ ID NO:3:

AGTTGAGGGG ACTTTCCCAG GC 22

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( v ) FRAGMENT TYPE: linear ( x i ) SEQUENCE DESCRIPTION: SEQ ID NO:4:

TCAACTCCCC TGAAAGGGTC CG 22